(12) United States Patent
Sanders et al.

(10) Patent No.: US 11,155,877 B2
(45) Date of Patent: Oct. 26, 2021

(54) NUCLEIC ACID DETECTION COMBINING AMPLIFICATION WITH FRAGMENTATION

(71) Applicant: Quest Diagnostics Investments LLC, Secaucus, NJ (US)

(72) Inventors: Heather R. Sanders, RSM, CA (US); Kevin Z. Qu, Lake Forest, CA (US); Charles M. Strom, San Clemente, CA (US); Richard A. Bender, Dana Point, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 67 days.

(21) Appl. No.: 16/165,400

(22) Filed: Oct. 19, 2018

(65) Prior Publication Data

US 2019/0100808 A1 Apr. 4, 2019

Related U.S. Application Data

(60) Continuation of application No. 15/712,448, filed on Sep. 22, 2017, now Pat. No. 10,106,857, which is a division of application No. 14/679,403, filed on Apr. 6, 2015, now Pat. No. 9,783,854, which is a continuation of application No. 12/035,356, filed on Feb. 21, 2008, now Pat. No. 8,999,634.

(Continued)

(51) Int. Cl.
*C12Q 1/68* (2018.01)
*C12Q 1/6886* (2018.01)
*C12Q 1/6806* (2018.01)

(52) U.S. Cl.
CPC ........ *C12Q 1/6886* (2013.01); *C12Q 1/6806* (2013.01); *C12Q 2600/118* (2013.01); *C12Q 2600/156* (2013.01); *C12Q 2600/16* (2013.01)

(58) Field of Classification Search
CPC ....................................................... C12Q 1/68
See application file for complete search history.

(56) References Cited

U.S. PATENT DOCUMENTS

| | | | |
|---|---|---|---|
| 5,079,352 A | 1/1992 | Gelfand et al. | |
| 5,135,717 A | 8/1992 | Renzoni et al. | |

(Continued)

FOREIGN PATENT DOCUMENTS

| | | | | |
|---|---|---|---|---|
| EP | 0539466 | 11/1996 | | |
| EP | 1033401 A2 * | 9/2000 | ............ | C07K 14/47 |

(Continued)

OTHER PUBLICATIONS

Stratagene (Gene Characterization Kits; 1988).*

(Continued)

*Primary Examiner* — Aaron A Priest
(74) *Attorney, Agent, or Firm* — Foley & Lardner LLP

(57) ABSTRACT

Provided herein are methods and compositions for detection of a nucleic acid target in a sample. The methods and compositions use primer directed amplification in conjunction with nucleic acid fragmentation. The methods have high sensitivity even in the presence of a large amount of non-target nucleic acid. Also provided are oligonucleotides and kits useful in the method. Exemplary nucleic acid targets are those with mutant gene sequence such as mutant sequence of the EGFR, APC, TMPRSS2, ERG and ETV1 genes.

10 Claims, 17 Drawing Sheets

Specification includes a Sequence Listing.

Related U.S. Application Data

(60) Provisional application No. 61/007,928, filed on Jun. 8, 2007, provisional application No. 60/926,611, filed on Apr. 27, 2007.

(56) References Cited

U.S. PATENT DOCUMENTS

| | | | |
|---|---|---|---|
| 5,502,167 A | 3/1996 | Waldmann et al. | |
| 5,512,441 A | 4/1996 | Ronai | |
| 5,580,990 A | 12/1996 | van den Berg et al. | |
| 5,652,099 A | 7/1997 | Conrad | |
| 5,714,327 A | 2/1998 | Houthoff et al. | |
| 5,840,482 A | 11/1998 | Gray et al. | |
| 5,981,725 A | 11/1999 | Vogelstein et al. | |
| 5,985,566 A | 11/1999 | Houthoff et al. | |
| 6,043,060 A | 3/2000 | Imanishi | |
| 6,127,126 A | 10/2000 | Vogelstein et al. | |
| 6,261,768 B1 | 7/2001 | Todd et al. | |
| 6,268,132 B1 | 7/2001 | Conrad | |
| 6,268,490 B1 | 7/2001 | Imanishi et al. | |
| 6,326,145 B1 | 12/2001 | Whitcombe et al. | |
| 6,630,301 B1 | 10/2003 | Gocke et al. | |
| 6,759,217 B2 | 7/2004 | Kopreski | |
| 6,902,891 B2 | 6/2005 | Laayoun et al. | |
| 2004/0106109 A1 | 6/2004 | Belly et al. | |
| 2005/0118625 A1* | 6/2005 | Mounts | C12Q 1/6837 435/6.14 |
| 2005/0202490 A1 | 9/2005 | Makarov et al. | |
| 2006/0147959 A1 | 7/2006 | Bell et al. | |
| 2006/0269956 A1 | 11/2006 | Sawyers et al. | |
| 2007/0010469 A1* | 1/2007 | Chan | C12Q 1/6886 514/44 A |
| 2007/0042982 A1* | 2/2007 | Bentwich | G16B 30/00 514/44 A |
| 2007/0269805 A1 | 11/2007 | Hogers | |
| 2008/0070797 A1* | 3/2008 | Mounts | B82Y 30/00 506/9 |
| 2011/0306043 A1* | 12/2011 | Fuchs | G01N 33/574 435/6.11 |

FOREIGN PATENT DOCUMENTS

| | | | | |
|---|---|---|---|---|
| GB | 2424886 A | * | 10/2006 | ............ C12Q 1/6883 |
| WO | WO 88/004300 | | 6/1988 | |
| WO | WO 98/039352 | | 11/1998 | |
| WO | WO 99/014226 | | 3/1999 | |
| WO | WO 00/056748 | | 9/2000 | |
| WO | WO 00/066604 | | 11/2000 | |
| WO | WO-0155312 A2 | * | 8/2001 | ............ C12Q 1/6883 |
| WO | WO-0157272 A2 | * | 8/2001 | ......... C12N 15/1089 |
| WO | WO-0157273 A2 | * | 8/2001 | .............. C07K 14/47 |
| WO | WO-0157275 A2 | * | 8/2001 | .............. C07K 14/47 |
| WO | WO-0157277 A2 | * | 8/2001 | ............ C12Q 1/6876 |
| WO | WO-0159063 A2 | * | 8/2001 | .............. C07K 14/47 |
| WO | WO-0173002 A2 | * | 10/2001 | ................ A61P 3/06 |
| WO | WO-2004033717 A1 | * | 4/2004 | ............ C12Q 1/6883 |
| WO | WO-2005000087 A2 | * | 1/2005 | ............ C12Q 1/6886 |
| WO | WO-2005094357 A2 | * | 10/2005 | .............. A61P 43/00 |
| WO | WO-2005111244 A2 | * | 11/2005 | ............ C12Q 1/6869 |
| WO | WO-2005117553 A2 | * | 12/2005 | ............ C12Q 1/6886 |
| WO | WO-2006070667 A1 | * | 7/2006 | ............ C12Q 1/6883 |
| WO | WO-2006108087 A2 | * | 10/2006 | ........ B01L 3/502753 |
| WO | WQ-2006108087 A2 | * | 10/2006 | ....... G01N 33/54366 |
| WO | WO-2007033187 A2 | * | 3/2007 | ......... A01K 67/0275 |

OTHER PUBLICATIONS

Asano et al., Detection of EGFR GeneMutation in Lung Cancer by Mutant-Enriched Polymerase Chain Reaction Assay, Clin Cancer Res. Jan. 1, 2006;12(1):43-8.*

Asano, H., et al., Detection of EGFR Gene Mutation in Lung Cancer by Mutant-Enriched PolymeraseChain Reaction Assay, Clinical Cancer Research 12(1)43-48 (2006).

Beilas et al., "Quantification of random genomic mutations," Nat. Methods, Apr. 2005 (epub Mar. 23, 2005), 2(4):285-290.

Beutler, et al., Interference of Heparin with the Polymerase Chain Reaction, BioTechniques 9:166 (1990).

Bibillo et al., The non-enzymatic hydrolysis of oligoribonucleotides VI. The role of biogenic polyamines, Nucleic Acids Res. 27:3931-3937 (1999).

Braasch, D.A., and Corey, D.R., Locked nucleic acid (LNA): fine-tuning the recognition of DNA and RNA, Chem. Biol. 8(1):1-7 (2001).

Carters et al., "Design and Use of Scorpians Fluorescent Signaling Molecules," Molecular Beacons: Signalling Nucleic Acid Probes, Methods and Protocols, Chapter 8, vol. 429, pp. 99-115, Dec. 2007.

Castells, A., et al., K-ras Mutations in DNA Extracted From the Plasma of Patients With Pancreatic Carcinoma: Diagnostic Utility and Prognostic Significance, J. Clin. Oncol. 17(2):578-584 (1999).

Chen et al. Detecting Tumor-related Alterations in Plasma or Serum DNA of Patients Diagnosed with Breast Cancer, Clin. Cancer Res. 5:2297-2303 (1999).

Coulet et al., Detection of Plasma Tumor DNA in Head and Neck Squamous Cell Carcinoma by Microsatellite Typing and p53 Mutation Analysis, Cancer Research, 60:707-711 (2000).

Coyle, et al., Role of Physical Activity in Modulating Breast Cancer Risk as Defined by APC and RASSF1A Promoter Hypermethylation in Nonmalignant Breast Tissue, Cancer Epidemiol. Biomarkers Prev. 16(2)192-196 (2007).

Diehl, et al., Detection and quantification of mutations in the plasma of patients with colorectal tumors, Proc. Nat. Acad. Science, 102:16368-16373 (2005).

Gautschi et al., Circulating Deoxyribonucleic Acid as Prognostic Marker in Non-Small-Cell Lung Cancer Patients Undergoing Chemotherapy, J. Clin. Oncol. 22:4157-4164 (2004).

Goebel et al., Circulating nucleic acids in plasma or serum (CNAPS) as prognostic and predictive markers in patients with solid neoplasias, Disease Markers 21:105-120 (2005).

Hafner, et al., Isothermal Amplification and Multimerization of DNA by Bst DNA Polymerase, Biotechniques Apr.;30(4):852-6, 858, 860 passim (2001).

Hagiwara et al., Quantitative Detection of p53 Mutations in Plasma DNA from Tobacco Smokers, Cancer Res. 66:(16)8309-8317 (2006).

Heid et al., Real time quantitative PCR, Genome Res. 6:986-994 (1996).

Herrera et al., Quantitative Analysis of Circulating Plasma DNA as a Tumor Marker in Thoracic Malignancies, Clin. Chem. 51:(1) 113-118 (2005).

Hibi et al., Molecular Detection of Genetic Alterations in the Serum of Colorectal Cancer Patients, Cancer Res. 58:1405-1407 (1998).

Hoque, M.O. et al., Detection of Aberrant Methylation of four Genes in Plasma DNA for the Detection of Breast Cancer, J. Clin. Oncol. 24(26)4262-4269 Epub Aug. 14, 2006 (2006).

Huang, X.H., et al., Codon 249 mutation in exon 7 of p53 gene in plasma DNA: maybe a new early diagnostic marker of hepatocellular carcinoma in Qidong risk area, China, World J. Gastroenterol. 9(4)692-695 (2003).

Jameson, D.M. and Eccleston, J.F., Fluorescent Nucleotide Analogs: Synthesis and Applications, Meth. Enzymol. 278:363-390 (1997).

Jenkins et al., "The restriction site mutation assay: a review of the methodology development and the current status of the technique," Mutagenesis, Sep. 1999, 14(5):439-448.

Kahn et al., "Rapid and sensitive nonradioactive detection of mutant K-ras genes via 'enriched' PCR amplification," Oncogene, Jun. 1991, 6(6):1079-1083.

Kimura, H. et al., Detection of Epidermal Growth Factor Receptor Mutations in Serum as a Predictor of the Response to Gefitinib in Patients with Non-Small-Cell Lung Cancer, Clin. Cancer Res. 12(13):3915-3921 (2006).

Kitabayashi et al., "Improvement of Reverse Transcription PCR by RNase H," Biosci. Biotechnol. Biochem., vol. 67, No. 11, pp. 2474-2476, 2003.

Le Roux, E., Gormally, E. and Hainaut, P., Somatic mutations in human cancer: applications in molecular epidemiology, Rev. Epidemiol. Sante Publique. 53:257-266 (2005).

(56) References Cited

OTHER PUBLICATIONS

Lynch, et al., Activating Mutations in the Epidermal Growth Factor Receptor Underlying Responsiveness of Non-Small-Cell Lung Cancer to Gefitinib, N Engl J Med 350(21) 2129-2139 (2004).
Mansfield et al., Nucleic acid detection using non-radioactive labeling methods, Mol. Cell. Probes 9:145-156 (1995).
Maxam, A.M. and Gilbert, W., Sequencing End-Labeled DNA with Base-Specific Chemical Cleavages, Meth. in Enzym. 65(1):499-560 (1980).
Myers et al., "The application of the restriction site mutation assay to the study of the induction of mutations in the tissues of rodents," Mutagenesis, May 1994, 9(3):175-177.
Newton, C.R., et al., Analysis of any point mutation in DNA. The amplification refractory mutation system (ARMS) Nucleic Acids Research 17(7):2503-2516 (1989).
Ohnishi, H., et al., A Simple and Sensitive Method for Detecting Major Mutations Within the Tyrosine Kinase Domain of the Epidermal Growth Factor Receptor Gene in Non-small-cell Lung Carcinoma, Diagnostic Molecular Pathology 15(2):101-108 (2006).
Oivanen, M., Kuusela, S. and Lönnberg, H., Kinetics and Mechanisms for the Cleavage and Isomerization of the Phosphodiester Bonds of RNA by Bronsted Acids and Bases, Chem Rev. (98):961-990 (1998).
Papadopoulou, E. et al., Cell-free DNA and RNA in Plasma as a New Molecular Marker for Prostate and Breast Cancer, Ann. N.Y. Acad. Sci. 1075:235-243 (2006).
Parsons et al., "Genotypic selection methods for the direct analysis of point mutations," Mutat. Res., Oct. 1997, 387(2):97-121.
Pathak et al., Circulating Cell-Free DNA in Plasma/Serum of Lung Cancer Patients as a Potential Screening and Prognostic Tool, Clinical Chem. 52(10):1833-1842 (2006).
Reiss et al., "Intracellular Association of a Mutant Insulin-like Growth Factor Receptor with Endogenous Receptors," Clin. Cancer Res., vol. 7, pp. 2134-2144, 2001.
Righetti et al., Emergence of p53 Mutant Cisplatin-resistant Ovarian Carcinoma Cells following Drug Exposure: Spontaneously Mutant Selection, Cell Growth & Differentiation, 10:473-478 (1999).
Saiki, "Amplification of Genomic DNA" in PCR Protocols, Innis et al., Eds., Academic Press, San Diego, CA pp. 13-20 (1990).
Shimansky et al., "Sensitive detection of K-ras mutations augments diagnosis of colorectal cancer metastases in the liver," Cancer Res. Oct. 15, 1999, 59(20):169-175.
Silva, J. M., et al., Tumor DNA in Plasma at Diagnosis of Breast Cancer Patients Is a Valuable Predictor of Disease-free Survival, Clin. Cancer Res. 8(12):3761-3766 (2002).
Sozzi et al. Analysis of Circulating Tumor DNA in Plasma at Diagnosis and during Follow-Up of Lung Cancer Patients, Cancer Res. 61:4675-4678 (2001).
Swisher, E.M., et al., Tumor-specific p53 sequences in blood and peritoneal fluid of women with epithelial ovarian cancer, American Journal of Obstetrics and Gynecology 193(3):662-667 (2005).
Thermo Electron Corporation, "User Guide for Automated purification of viral RNA and DNA from biofluid samples with KingFisher instrument and MagMAXTM-96 Viral RNA Isolation Kit," Ambion—the RNA Company, Sep. 2, 2006.
Trawick et al., Inorganic Mimics of Ribonucleases and Ribozymes: From Random Cleavage to Sequence-Specific Chemistry to Catalytic Antisense Drugs, Chem Rev. 98:939-960 (1998).
Tyagi, et al., Multicolor molecular beacons for allele discrimination, Nature Biotechnology 16:49-53 (1998).
Vermulst et al., "Quantification of random mutations in the mitochondrial genome," Methods, Dec. 2008 (epub Oct. 21, 2008), 46(4):263-268.
Ward et al., "Restriction Endonuclease-Mediated Selective Polymerase Chain Reaction: A Novel Assay for the Detection of K-ras Mutations in Clinical Samples," American Journal of Pathology, vol. 153, No. 2, pp. 373-379, Aug. 1998.
Wharam, et al., Specific detection of DNA and RNA targets using a novel isothermal nucleic acid amplification assay based on the formation of a three-way junction structure, Nucleic Acids Res. 29(11):E54-E54 (2001).
Whitcombe, D. et al., Detection of PCR products using self-probing amplicons and fluorescence, Nature Biotechnology 17:804-807 (1999).
Zhu et al., Directly labeled DNA probes using fluorescent nucleotides with different length linkers, Nucl. Acids Res. 22:3418-3422 (1994).
Office Action dated Apr. 8, 2010 in U.S. Appl. No. 12/035,356.
Office Action dated Jul. 7, 2010 in U.S. Appl. No. 12/035,356.
Office Action dated Dec. 23, 2010 in U.S. Appl. No. 12/035,356.
Office Action dated Mar. 1, 2011 in U.S. Appl. No. 12/035,356.
Office Action dated Sep. 19, 2013 in U.S. Appl. No. 12/035,356.
Office Action dated Apr. 21, 2014 in U.S. Appl. No. 12/035,356.
Notice of Allowance dated Dec. 3, 2014 in U.S. Appl. No. 12/035,356.
Office Action dated Feb. 13, 2017, in U.S. Appl. No. 14/679,403.
Notice of Allowance dated Jun. 6, 2017, in U.S. Appl. No. 14/679,403.

* cited by examiner

Wild-type EGFR Gene Sequence

```
CCACACGGACTTTATAACAGGCTTTACAAGCTTGAGATTCTTTTATCTAAATAATCAGTGTGATTCGTGGA
GCCCAACAGCTGCAGGGCTGCGGGGGCGTCACAGCCCCCAGCAATATCAGCCTTAGGTGCGGCTCCACAGC
CCCAGTGTCCCTCACCTTCGGGGTGCATCGCTGGTAACATCCACCCAGATCACTGGGCAGCATGTGGCACC
ATCTCACAATTGCCAGTTAACGTCTTCCTTCTCTCTGTCATAGGGACTCTGGATCCCAGAAGGTGAGAA
AGTTAAAATTCCCGTCGCTATCAAGGAATTAAGAGAAGCAACATCTCCGAAAGCCAACAAGGAAATCCTCG
ATGTGAGTTTCTGCTTTGCTGTGTGGGGGTCCATGGCTCTGAACCTCAGGCCCACCTTTTCTCATGTCTGG
CAGCTGCTCTGCTCTAGACCCTGCTCATCTCCACATCCTAAATGTTCACTTTCTATGTCTTTCCCTTTCTA
GCTCTAGTGGGTATAACTCCCTCCCCTTAGAGACAGCACTGGCCTCTCCCATGCTGGTATCCACCCCAAAA
GGCTGGAAACAGGCAATTACTGGCATCTACCCAGCACTAGTTTCTTGACACGCATGATGAGTGAGTGCTCT
TGGTGAGCCTGGAGCATGGGTATTGTTTTTGGTATTTTTTGGATGAAGAAATGGAGGCATAAAGAAATTGG
CTGACCCTTATATGGCTGGGATAGGGTTTAAGCCCCTTGTTATTTCTGACTCTGAAACTT
```

FIGURE 2A

EGFR Exon 19 Deletion Mutant Gene Sequence (E746_A750del)

CCACACGGACTTTATAACAGGCTTTACAAGCTTGAGATTCTTTTATCTAAATAATCAGTGTGATTCGTGGA
GCCCAACAGCTGCAGGGCTGCGGGGGCGTCACAGCCCCCAGCAATATCAGCCTTAGGTGCGGCTCCACAGC
CCCAGTGTCCCTCACCTTCGGGGTGCATCGCTGGTAACATCCACCCAGATCACTGGGCAGCATGTGGCACC
ATCTCACAATTGCCAGTTAACGTCTTCCTTCTCTCTGTCATAGGGACTCTGGATCCCAGAAGGTGAGAA
AGTTAAAATTCCCGTCGCTATCAAAACATCTCCGAAAGCCAACAAGGAAATCCTCGATGTGAGTTTCTGCT
TGCTGTGTGGGGGTCCATGGCTCTGAACCTCAGGCCCACCTTTTCTCATGTCTGGCAGCTGCTCTGCTCT
AGACCCTGCTCATCTCCACATCCTAAATGTTCACTTTCTATGTCTTTCCCTTTCTAGCTCTAGTGGGTATA
ACTCCCTCCCCTTAGAGACAGCACTGGCCTCTCCCATGCTGGTATCCACCCCAAAAGGCTGGAAACAGGCA
ATTACTGGCATCTACCCAGCACTAGTTTCTTGACACGCATGATGAGTGAGTGCTCTTGGTGAGCCTGGAGC
ATGGGTATTGTTTTTGGTATTTTTTGGATGAAGAAATGGAGGCATAAAGAAATTGGCTGACCCTTATATGG
CTGGGATAGGGTTTAAGCCCCTTGTTATTTCTGACTCTGAAACTT

FIGURE 2B

Region surrounding and including insertion in APC exon 16

CCAGCTCCGTTCAGAGTGAACCATGCAGTGGAATGGTAAGTGGCATTATAAGCCCCAGTGATCTTCCAGATAGCC
CTGGACAAACCATGCCACCAAGCAGAAGTAAAACA CCTC CACCA CCTCCTC AAACAGCTCAAACCAAGCGAGAA
GTACCTAAAAATAAAGCACCTACTGCTGAAAAGAGAGAGAGTGGACCTAAGCAAGCTGCAGTAAATGCTGCAGTT
CA GAGG GTCCAGGTTCTTCCAGATGCTGATACTTTATTACATTTTGCCACGGAAAGTACTCCAGATGGATTTTCT
TGTTCATCCAGCCTGAGTGCTCTGAG CCTC GATGAGCCATTTATACAGAAAGATGTGGAATTAAGAATAATGTGC
ATGTGTCTTTATAGCAGCATGATTTATACTCATTTGGGTATATACCCAGTAATGGGATGGCTGGGTCAAATGGTA
TTTCTAGTTCTAGATCCCT GAGG AATCGCCACACTGA CTTCCACAATGGTTGAACTAG TTTACAGTCCCACCAAG
AAAATGTGGCACATATACACCATGGAATACTATGCAGCCATAAAAAATGATGAGTTCATAT CCTTTGTAGGGACA
TGGATG AAATTGGAAACCATCATTCTCAGTAAACTATCGCAAGAACAAAAAACCAAACACCGCATATTCTCACTT
ATAGGTGGGAATTGAACAATGAGATCACATGGACACAGGAAGGGGAATATCACACTCTGGGGACTGTGGTGGGGT
CGGGG GAGG GGG GAGG GATAGCATTGGGAGATATACCTAATGCTAGATGACACATTAGTGGGTGCAGCGCAGCA
TGGCACATGTATACATATGTAACTAACCTGCACAATGTGCACATGTACCCTAAAACTTAGAGTATAATAAAAAAA
AAAAAAAAAAAAATAACAATAAATGAGATAAAATCTAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAGA
ATAATG CCTC CAGTTCAGGAAAATGACAATGGGAATGAAACAGAATCAGAGCAGCCTAAAGAATCAAATGAAAAC
CAAGAGAAA GAGG CAGAAAAAACTATTGATTCTGAAAAGGACCTATTAGATGATTCAGATGATGATGATATTGAA
ATACTAGAAGAATGTATTATTTCTGCCATGCCAACAAAGTCATCACGTAAAGCAAAAAAGCCAGCCCAGACTGCT
TCAAAATTA CCTC CACCTGTGGCAAGGAAACCAAGTCAGCTGCCTGTGTACAAACTTCTACCATCACAAAACAGG
TTGCAACCCCAAAAGCATGTTAGTTTTACACCGGGGGATGATATGCCACGGGTGTATTGTGTTGAAGGGACACCT
ATAAACTTTTCCACAGCTACATCTCTAAGTGATCTAACAATCGAATCC CCTC CAAATGAGTTAG

FIGURE 4

Region surrounding and including insertion in APC exon 16

CCAGCTCCGTTCAGAGTGAACCATGCAGTGGAATGGTAAGTGGCATTATAAGCCCCAGTGATCTTCCAGATAGCC
CTGGACAAACCATGCCACCAAGCAGAAGTAAAACA`CCTC`CACCA`CCTCCTC`AAACAGCTCAAACCAAGCGAGAA
GTACCTAAAAATAAAGCACCTACTGCTGAAAAGAGAGAGAGTGGACCTAAGCAAGCTGCAGTAAATGCTGCAGTT
CA`GAGG`GTCCAGGTTCTTCCAGATGCTGATACTTTATTACATTTTGCCACGGAAAGTACTCCAGATGGATTTTCT
TGTTCATCCAGCCTGAGTGCTCTGAG`CCTC`GAT`GAGCCATTTATACAGAAAGATG`TGGAATTAAGAATAATGTGC
ATGTGTCTTTATAGCAGCATGATTTATACTCATTTGGGTATATACCCAGTAATGGGATG`GCTGGGTCAAATGGTA`
`TTTC`TAGTTCTAGATCCCT`GAGG`AATCGCCACACTGACTTCCACAATGGTTGAACTAGTTTACAGTCCCACCAAG
AAAATGTGGCACATATACACCATGGAATACTATGCAGCCATAAAAAATGATGAGTTCATATCCTTTGTAGGGACA
TGGATGAAATTGGAAACCATCATTCTCAGTAAACTATCGCAAGAACAAAAACCAAACACCGCATATTCTCACTT
ATAGGTGGGAATTGAACAATGAGATCACATGGACACAGGAAGGGGAATATCACACTCTGGGGACTGTGGTGGGGT
CGGGG`GAGG`GGG`GAGG`GATAGCATTGGGAGATATACCTAATGCTAGATGACACATTAGTGGGTGCAGCGCAGCA
TGGCACATGTATACATATGTAACTAACCTGCACAATGTGCACATGTACCCTAAAACTTAGAGTATAATAAAAAAA
AAAAAAAAAAAATAACAATAAATGAGATAAAATCTAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAGA
ATAATG`CCTC`CAGTTCAGGAAAATGACAATGGGAATGAAACAGAATCAGAGCAGCCTAAAGAATCAAATGAAAAC
CAAGAGAAA`GAGG`CAGAAAAAACTATTGATTCTGAAAAGGACCTATTAGATGATTCAGATGATGATGATATTGAA
ATACTAGAAGAATGTATTATTTCTGCCATGCCAACAAAGTCATCACGTAAAGCAAAAAAGCCAGCCCAGACTGCT
TCAAAATTA`CCTC`CACCTGTGGCAAGGAAACCAAGTCAGCTGCCTGTGTACAAACTTCTACCATCACAAAACAGG
TTGCAACCCCAAAAGCATGTTAGTTTTACACCGGGGGATGATATGCCACGGGTGTATTGTGTTGAAGGGACACCT
ATAAACTTTTCCACAGCTACATCTCTAAGTGATCTAACAATCGAATCC`CCTC`CAAATGAGTTAG

FIGURE 6

Wild-type EGFR Gene Sequence (exon 21)

TGACCCTGAATTCGGATGCAGAGCTTCTTCCCATGATGATCTGTCCCTCACAGCAGGGTCTTCTCTGTTT
CAGGGCATGAACTACTTGGAGGACCGTCGCTTGGTGCACCGCGACCTGGCAGCCAGGAACGTACTGGTGA
AAACACCGCAGCATGTCAAGATCACAGATTTTGGGCTGGCCAAACTGCTGGGTGCGGAAGAGAAAGAATA
CCATGCAGAAGGAGGCAAAGTAAGGAGGTGGCTTTAGGTCAGCCAGCATTTTCCTGACACCAGGGACCAG
GCTGCCTTCCCACTAGCTGTATTGTTTAACACATGCAGGGGAGGATGCTCTCCAGACATTCTGGGTGAGC
TCGCAGCAGCTGCTGCTGGCAGCTGGGTCCAGCCAGGGTCTCCTGGTAGTGTGAGCCAGAGCTCTGAGGT
TTCACTCTGGCCTGCTGGGCTCCTAGCAGCCACCAACCCATGATGCTGGGCCCTGAAAACACACGCAGAC
CTGGATGAGTGAGGCCACTGGGCACAACCAGGGC

L858R mutant EGFR Gene Sequence (exon 21)

TGACCCTGAATTCGGATGCAGAGCTTCTTCCCATGATGATCTGTCCCTCACAGCAGGGTCTTCTCTGTTT
CAGGGCATGAACTACTTGGAGGACCGTCGCTTGGTGCACCGCGACCTGGCAGCCAGGAACGTACTGGTGA
AAACACCGCAGCATGTCAAGATCACAGATTTTGGGCGGGCCAAACTGCTGGGTGCGGAAGAGAAAGAATA
CCATGCAGAAGGAGGCAAAGTAAGGAGGTGGCTTTAGGTCAGCCAGCATTTTCCTGACACCAGGGACCAG
GCTGCCTTCCCACTAGCTGTATTGTTTAACACATGCAGGGGAGGATGCTCTCCAGACATTCTGGGTGAGC
TCGCAGCAGCTGCTGCTGGCAGCTGGGTCCAGCCAGGGTCTCCTGGTAGTGTGAGCCAGAGCT

FIGURE 8

Wild Type TMPRSS2

TGTCGCCCTGGACCCTGGGACACCGCCTCCTGAGATTAAAGCGAGAGCCAGGGCGGGCCGGGCCGAGT
AGGCGCGAGCTAAGCAGGAGGCGGAGGCGGAGGCGGAGGGCGAGGGGCGGGGAGCGCCGCCTGGAGCG
CGGCAGGTCATATTGAACATTCCAGATACCTATCATTACTCGATGCTGTTGATAACAGCAAGATGGCT
TTGAACTCAGGGTCACCACCAGCTATTGGACCTTACTATGAAAACCATGGATACCAACCGGAAAACCC
CTATCCCGCACAGCCCACTGTGGTCCCCACTGTCTACGAGGTGC

Wild Type ERG

CCAAAAGCAAGACAAATGACTCACAGAGAAAAAAGATGGCAGAACCAAGGGCAACTAAAGCCGTCAGGT
TCTGAACAGCTGGTAGATGGGCTGGCTTACTGAAGGACATGATTCAGACTGTCCCGGACCCAGCAGCT
CATATCAAGGAAGCCTTATCAGTTGTGAGTGAGGACCAGTCGTTGTTTGAGTGTGCCTACGGAACGCCA
CACCTGGCTAAGACAGAGATGACCGCGTCCTCCTCCAGCGACTATGGACAGACTTCCAAGATGAGCCCA
CGCGTCCCTCAGCAGGATTGGCTGTCTCAACCCCAGCCAGGGTCACCATCAAAATGGAATGTAACCCT
AGCCAGGTGAATGGCTCAAG

TMPRSS2:ERG fusion transcript

TGTCGCCCTGGACCCTGGGACACCGCCTCCTGAGATTAAAGCGAGAGCCAGGGCGGGCCGGGCCGAGT
AGGCGCGAGCTAAGCAGGAGGCGGAGGCGGAGGCGGAGGGCGAGGGGCGGGGAGCGCCGCCTGGAGCG
CGGCAGGAAGCCTTATCAGTTGTGAGTGAGGACCAGTCGTTGTTTGAGTGTGCCTACGGAACGCCACA
CCTGGCTAAGACAGAGATGACCGCGTCCTCCTCCAGCGACTATGGACAGACTTCCAAGATGAGCCCAC
GCGTCCCTCAGCAGGATTGGCTGTCTCAACCCCAGCCAGGGTCACCATCAAAATGGAATGTAACCCT
AGCCAGGTGAATGGCTCAAG

FIGURE 10

Wild Type TMPRSS2

TGTCGCCCTGGACCCTGGGACACCGCCTCCTGAGATTAAAGCGAGAGCCAGGGCGGGCCGGGCCGAGTAGG
CGCGAGCTAAGCAGGAGGCGGAGGCGGAGGCGGAGGGCGAGGGGCGGGGAGCGCCGCCTGGAGCGCGGCAG
GTCATATTGAACATTCCAGATACCTATCATTACTCGATGCTGTTGATAACAGCAAGATGGCTTTGAACTCA
GGGTCACCACCAGCTATTGGACCTTACTATGAAAACCATGGATACCAACCGGAAAACCCCTATCCCGCACA
GCCCACTGTGGTCCCCACTGTCTACGAGGTGC

Wild Type ETV1

TGCGAAGAGCAGCAGCATGGATGGATTTTATGACCAGCAAGTGCCTTACATGGTCACCAATAGTCAGCGTG
GGAGAAATTGTAACGAGAAACCAACAAATGTCAGGAAAAGAAAATTCATTAACAGAGATCTGGCTCATGAT
TCAGAAGAACTCTTTCAAGATCTAAGTCAATTACAGGAAACATGGCTTGCAGAAGCTCAGGTACCTGACAA
TGATGAGCAGTTTGTACCAGACTATCAGGCTGAAAGTTTGGCTTTTCATGGCCTGCCACTGAAAATCAAGA
AGAACCCCACAGTCCATGTTCAGAAATCAGCTCTGCCTGCAGTCAAGAACAGCCCTTTAAATTCAGCTAT

TMPRSS2:ETV1 fusion transcript

TGTCGCCCTGGACCCTGGGACACCGCCTCCTGAGATTAAAGCGAGAGCCAGGGCGGGCCGGGCCGAGTAGG
CGCGAGCTAAGCAGGAGGCGGAGGCGGAGGCGGAGGGCGAGGGGCGGGGAGCGCCGCCTGGAGCGCGGCAG
CTCAGGTACCTGACAATGATGAGCAGTTTGTACCAGACTATCAGGCTGAAAGTTTGGCTTTTCATGGCCTG
CCACTGAAAATCAAGAAAGAACCCCACAGTCCATGTTCAGAAATCAGCTCTGCCTGCAGTCAAGAACAGCC
CTTTAAATTCAGCTAT

FIGURE 12

NUCLEIC ACID DETECTION COMBINING AMPLIFICATION WITH FRAGMENTATION

CROSS-REFERENCE TO RELATED APPLICATIONS

The present application is a Continuation of U.S. application Ser. No. 15/712,448, filed Sep. 22, 2017, which is a Divisional of U.S. application Ser. No. 14/679,403, filed Apr. 6, 2015, which is a Continuation of U.S. application Ser. No. 12/035,356, filed Feb. 21, 2008, which claims priority to U.S. Provisional Patent Application No. 60/926,611, Titled: Nucleic Acid Detection Combining Amplification With Fragmentation, filed Apr. 27, 2007 and U.S. Provisional Patent Application No. 61/007,928, Titled: Nucleic Acid Detection Combining Amplification With Fragmentation, filed Jun. 8, 2007, which are incorporated herein by reference.

The instant application contains a Sequence Listing which has been submitted in ASCII format via EFS-WEB and is hereby incorporated by reference in its entirety. Said ASCII copy, created on Sep. 18, 2018, is named sequence.txt and is 17 KB.

FIELD OF THE INVENTION

Provided herein are methods and compositions for detecting target nucleic acid such as mutant nucleic acid. The methods and compositions combine amplification with nucleic acid fragmentation, are useful for detecting very low amounts of target nucleic acids, even in the presence of large amounts of non-target nucleic acids.

BACKGROUND OF THE INVENTION

Although nucleic acid assays are known to offer a high degree of specificity, there are limits in the sensitivity of such assays, particularly when the target nucleic acid to be detected is present in relatively low quantities compared to non-target nucleic acid. In the case of cancer, the ability to detect the presence of a small amount of a cancer specific mutant nucleic acid allows for early cancer diagnosis and offers the possibility of more effective therapeutic intervention. However, detection can be challenging if the sample of nucleic acid being tested has very little of the mutant nucleic acid and if there is an excess of normal nucleic acid in the sample. Although a tumor biopsy may contain significant mutant nucleic acids, a plasma sample from a cancer patient may contain one or only a few copies of a mutant nucleic acid of interest. Amplification methods such as PCR may detect a few copies of a mutant nucleic acid, however, the abundance of normal nucleic acid in samples such as plasma can interfere.

Focus has been placed on identifying tumor-derived mutations in circulating DNA found in plasma or serum of solid tumor patients as a noninvasive and early diagnostic tool. Confirmed reports of the presence of solid tumor-derived mutations found in circulating DNA include, but are not limited to, patients with colorectal tumors, pancreatic cancer, breast cancer, head and neck squamous cell carcinoma, and lung cancer (Hibi et al. 1998, Chen et al. 1999, Diehl et al. 2005, Coulet et al. 2000, Hagiwara 2006, Kimura et al. 2006).

Reports have also demonstrated that cancer patients show elevated levels of circulating DNA and have proposed use of DNA quantification as prognostic and diagnostic factors (Gautschi et al. 2004, Goebel et al. 2005, Sozzi et al. 2001, Herrera et al. 2005, Pathak et al. 2006). This has led to efforts to describe the origin of such elevated levels of DNA. While still under investigation, the sharp increase in circulating DNA is not likely attributed to DNA released from tumor cells. In fact, analysis of mutations present in the plasma of patients with colorectal tumors revealed that the levels of mutations found in circulating DNA did not increase proportionally with the overall elevated levels of circulating DNA (Diehl et al. 2005). Thus while some cancer patients show elevated levels of plasma DNA, detection of tumor-derived mutations will require the ability to detect very few mutations in the presence of larger amounts of wild type DNA.

A number of strategies have been described for detecting low copy number nucleic acid targets. Methods including allele-specific PCR of p53 and ABL kinase domain mutations have demonstrated sensitivities ranging from 0.1-0.01% and in one mutation, 0.001% (Righetti et al. 1999, Coulet et al. 2000, and Kang et al 2006). Ohnishi, H., et al. reported a method of amplification using a mutation specific primer that spans a deletion site and does not anneal to the wild-type sequence. Ohnishi, H., et al., 15(2) Diagnostic Molecular Pathology 101-108 (2006). Mutation specific primers of the Scorpion type also have been reported. Kimura, H. et al., 12(13) Clinical Cancer Research 3915-3921 (2006); Newton, C. R., et al., 17(7) Nucleic Acids Research 2503-2516 (1989); and Whitcombe, D. et al., 17 Nature Biotechnology 804-807 (1999) (describing Scorpion ARMS primers and strategies for primer design). Methods that enrich mutant nucleic acid by digesting wild-type DNA with restriction enzymes prior to amplification have been reported. Asano, H., et al., 12(1) Clinical Cancer Research 43-48 (2006); Gocke, C., et al., U.S. Pat. No. 6,630,301. The Asano et al., method uses multiple PCR reactions. A first PCR reaction is used to remove an upstream restriction enzyme recognition site. Following the first PCR, a restriction digestion is performed. After digestion, a second PCR reaction is used to amplify the target sequence.

SUMMARY OF THE INVENTION

Provided herein are methods and compositions for detecting target nucleic acids at very low levels and in the presence of large amounts of non-target nucleic acids. Generally, a target and non-target nucleic acid are distinguished by the presence or absence of a fragmentation site, such as a restriction enzyme recognition site. By differentiating the target and non-target by a fragmentation site, the methods and compositions used herein can be used with various nucleic acid detection methods known in the art, such as PCR.

As used herein, the term "target" nucleic acid refers to a nucleic acid which contains an allele or a mutant nucleic acid sequence. A mutant nucleic acid sequence may be any mutant sequence including but not limited to substitution, insertion, deletion, and translocation.

As used herein, the term "non-target" or "other" nucleic acid used in reference to a target nucleic acid means a nucleic acid that does not contain the target sequence. For example, a non-target nucleic acid of a target nucleic acid encoding an allelic sequence encompasses nucleic acid that contains an alternative allele. The non-target of a nucleic acid containing a mutant sequence is a nucleic acid that contains normal or wild-type nucleic acid sequence with respect to the mutant sequence.

As used herein, the term "locked nucleic acid" or "LNA" refers to bicyclic nucleic acid analogs contain one or more 2'-O, 4'-C methylene linkage(s), which effectively locks the furanose ring in a C3'-endo conformation. This methylene linkage restricts the flexibility of the ribofuranose ring and locks the structure into a rigid bicyclic formation. Because of its structural conformation, locked nucleic acids demonstrate a much greater affinity and specificity to their complementary nucleic acids than do natural DNA counterparts and increases the thermal and chemical stability of a primer/target nucleic acid duplex. LNAs will hybridize to complementary nucleic acids even under adverse conditions, such as under low salt concentrations and in the presence of chaotropic agents. According to one aspect of the invention, locked nucleic acids increase the melting point of the primer/target nucleic acid duplex by about 3 to about 8° Celsius per locked nucleic acid base incorporated in the primer. The basic structural and functional characteristics of LNAs and related analogues are disclosed in various publications and patents, including WO 99/14226, WO 00/56748, WO 00/66604, WO 98/39352, U.S. Pat. Nos. 6,043,060, and 6,268,490; see also, Braasch et al., "Locked nucleic acid (LNA): fine-tuning the recognition of DNA and RNA," Chem. Biol. 8(1):1

Locked nucleic acid bases may be interspersed throughout a strand of a primer, placed consecutively or placed singularly in predetermined locations. In one embodiment, the mutation specific primer comprises a locked nucleic acid base at its 3' terminus. In another embodiment, the mutation specific primer comprises a locked nucleic acid base at its N−1 (i.e., penultimate) base. The mutant base may be a locked nucleic acid.

In one aspect, provided herein is a method for detecting the presence or absence of a target nucleic acid by testing a sample that potentially contains the target nucleic acid in the presence of non-target nucleic acid, the method includes: a) fragmenting the sample nucleic acid under conditions such that a subsequent amplification directed to the target nucleic acid results in an increased detection of the target nucleic acid over the non-target nucleic acid as compared to amplification without fragmentation; b) amplifying the target nucleic acid with a pair of primers, where a first primer is specific for the target nucleic acid; and c) detecting the presence or absence of an amplification product, which indicates the presence or absence of the target nucleic acid in the sample.

In another aspect, provided herein is a method for diagnosing a cancer or detecting the presence of a tumor cell by determining if an individual has a mutant sequence associated with the cancer or tumor cell type, the method includes: a) obtaining a sample including nucleic acid from the individual; b) fragmenting the sample nucleic acid under conditions such that a subsequent amplification directed to the target nucleic acid results in an increased detection of the target nucleic acid over the non-target nucleic acid as compared to amplification without fragmentation; c) amplifying the target nucleic acid with a pair of primers, where a first primer is specific for the target nucleic acid; and d) detecting the presence or absence of an amplification product containing the mutant sequence, where diagnosis of cancer is determined by the presence absence or amount of amplification product containing the mutant sequence.

In yet another aspect, provided herein is a method for determining prognosis with cancer by determining if an individual has a mutant sequence associated with the cancer, the method includes: a) obtaining a sample containing nucleic acid from the individual; b) fragmenting the mutant nucleic acid under conditions such that a subsequent amplification directed to the mutant nucleic acid results in an increased detection of the mutant nucleic acid over the non-mutant nucleic acid as compared to amplification without fragmentation; c) amplifying the mutant nucleic acid with a pair of primers, where a first primer is specific for the mutant nucleic acid; and d) detecting the presence, absence and/or amount of an amplification product containing the mutant sequence, where the likelihood of an outcome in the individual is associated with the presence and or amount of mutant nucleic acid sequence.

In still yet another aspect, provided herein is a method for determining drug sensitivity of an individual diagnosed with cancer, the method includes: a) obtaining a sample comprising nucleic acid from the individual; b) fragmenting the mutant nucleic acid under conditions such that a subsequent amplification directed to the mutant nucleic acid results in an increased detection of the mutant nucleic acid over the non-mutant nucleic acid as compared to amplification without fragmentation; c) amplifying the mutant nucleic acid with a pair of primers, where a first primer is specific for the mutant nucleic acid; d) detecting the presence, absence and/or amount of an amplification product containing the mutant sequence; and e) relating the presence, absence and/or amount of an amplification product containing the mutant sequence to cancer drug sensitivity. Some examples of mutations that affect drug sensitivity which may be targeted by the assay methods described herein are described in Lynch, et al., 350(21) NEJM 2129-2139 (2004); Bell, et al., US Patent App. No. 20060147959 (2005) (determining tyrosine kinase inhibitor, i.e., gefitinib and erlotinib sensitivity by detecting EGFR mutations); and Sawyers, et al., U.S. Patent Appl. No. 2006/0269956 (describing mutations that affect drug resistance to BCR-ABL kinase activity inhibitors typically used to treat CML due to the T315I mutation in the Abl gene).

In certain embodiments of the aspects provided herein, the mutated nucleic acid sequence is due to a deletion, insertion, substitution and/or translocation or combinations thereof. In preferred embodiments, fragmentation of nucleic acid sequence in which cleavage of wild-type sequence is with a restriction enzyme. Such pre-amplification digestion treatment allows for fragmentation to destroy or substantially decrease the number of wild-type sequences that might be amplified. In yet more preferred embodiments, the fragmentation using a restriction enzyme is combined with the use of a mutation specific primer (or mutated sequence primer).

In preferred embodiments, a mutated sequence destroys or disrupts a restriction enzyme recognition site present in the corresponding wild-type sequence and that a mutation specific primer can be designed to bind to the mutated version of the sequence and not its wild-type counterpart. For example a mutation specific primer can overlap a border region, which is a region that contains portions of both a wild-type sequence adjacent to a portion of the mutated sequence. In further examples, if a mutation is the result of a deletion, such as the 15 bp deletion in exon 19 of the Epidermal Growth Factor Receptor (EGFR) gene (E746_A750del), a mutation specific primer could be designed, as illustrated in FIG. 1, so as to span a new site in the DNA which arises from the deletion. Other methods of detecting EGFR nucleic acid are described in U.S. Pat. No. 6,759,217 (which describes detecting EGFR nucleic acid in plasma or serum), U.S. Pat. Nos. 6,127,126 and 5,981,725 (both disclose detecting nucleic acid encoding an EGFR mutant protein type II for a mutation in which a portion of the extracellular domain of EGFR is deleted). If a mutation is due to an insertion, a mutation specific primer could be designed to span either or both junctions where the inserted sequence is adjacent to wild-type sequence. If a mutation is due to one or more substitutions, then a mutation specific primer could be designed to span any or all of the substitutions. If a mutation is due to a translocation, then a mutation specific primer could be designed to span one or both junctions of the translocated sequence, in any region where the sequence is altered by the translocation. These examples are merely exemplary and provide guidance to one of skill in the art to design various permutations of primers that would anneal to a mutated sequence and not a wild-type sequence which are appropriate for the methods and compositions provided herein.

In one approach, a sample is assayed for the presence or absence of a mutated sequence by amplification and detection of the resulting amplification products. In a preferred embodiment, amplification of target nucleic acids is accomplished by polymerase chain reaction (PCR).

Single or multiple mutant sequences can be assayed. Amplification of multiple mutant sequences can be performed simultaneously in a single reaction vessel, e.g., multiplex PCR. In this case, probes may be distinguishably labeled and/or amplicons may be distinguishable by size differentiation. Alternatively, the assay could be performed in parallel in separate reaction vessels. In such later case, the probes could have the same label.

In certain embodiments of the aspects provided herein, the methods further comprise a nucleic acid extraction step. Various extraction nucleic acid methods are known in the art which can be employed with the methods and compositions provided herein such as lysis methods (such as alkaline lysis), phenol:chloroform and isopropanol precipitation. Nucleic acid extraction kits can also be used. Preferably, the extraction method is Agencourt Genfind™, Roche Cobas® or phenol:chloroform extraction using Eppendorf Phase Lock Gels®. More preferably the nucleic acid is extracted using Agencourt Genfind™

Also provided are exemplary oligonucleotides useful in the methods and kits described herein.

The following mutated sequences can be detected with the methods and compositions provided herein. The methods outlined for detection of specific deletion mutations, insertion mutations, point mutations and fusion transcripts can be applied to any biomarker which may be used with fragmentation, particularly when a restriction digestion recognition site is disrupted. Embodiments of specific primer designs are described below but the sequence will vary to fit the mutation to be detected. Restriction enzyme digestion sites will also depend on the sequence of the wild-type sequence as compared to the mutated nucleic acid or fusion transcript. The frequency of various restriction sites found in DNA virtually ensures that a site unique to the wild-type DNA of interest can be found for any mutation detection assay, thus this methodology is applicable to a wide array of cancer biomarkers.

In one approach, a mutation specific primer is designed for detecting a deletion mutation. Mutation specific primer can be designed to span the deleted region such that the primer contains wild-type sequence that lies 5' and 3' of the deleted region or the complement thereof. Thus, the mutation specific primer cannot bind to the wild-type sequence and cannot produce an amplicon.

In one approach, a mutation specific primer is designed for detecting an insertion mutation. A mutation specific primer can be designed to span all or a portion of the inserted region such that the primer includes all or a part of the inserted region. A primer could be designed to span the either or both junctions of the inserted sequence, for example, the primer sequence would include a portion of wild-type sequence that is adjacent to the inserted sequence or the complement thereof. Thus, the mutation specific primer is not complementary to the wild-type sequence and cannot produce an amplicon.

In one approach, a mutation specific primer is designed for detecting one or more substitution mutations. A mutation specific primer can be designed to include one or more substitutions or the complement thereof. For example, the 3' nucleotide of the primer can be designed such that it contains the mutated base pair and does not bind hybridize, or base pair, in the wild-type gene and thus cannot elongate.

In one approach, a mutation specific primer is designed for detecting one or more translocation mutations. A mutation specific primer can be designed to span the junction of the translocation or the complement thereof. A primer pair could be designed to so that one primer is upstream of the translocation junction and the second is downstream of the junction. Thus, when the primer pair is used on wild-type sequence, no amplification products will be produced because the locations of the primers relative to each other are cannot be amplified. However, when the translocation is present, the primers are in close enough proximity of each other such that an amplification product can be produced. For example, the primer can be designed to include a portion of the first gene and a portion of the second gene, where the genes are located on different chromosomes in wild-type form but are adjacent to one another in the mutated form.

In certain embodiments, at least one primer of each primer pair in the amplification reaction is labeled with a detectable moiety. Thus, following amplification, the various target segments can be identified by size and color. The detectable moiety is preferably a fluorescent dye. In some embodiments, different pairs of primers in a multiplex PCR may be labeled with different distinguishable detectable moieties. Thus, for example, HEX and FAM fluorescent dyes may be present on different primers in multiplex PCR and associated with the resulting amplicons. In other embodiments, the forward primer is be labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length. Thus, in certain embodiments, at least two different fluorescent dyes are used to label different primers used in a single amplification. In still another embodiment, control primers can be labeled with one moiety, while the patient (or test sample) primers can be labeled with a different moiety, to allow for mixing of both samples (post PCR) and the simultaneous detection and comparison of signals of normal and test sample. In a modification of this embodiment, the primers used for control samples and patient samples can be switched to allow for further confirmation of results.

Analysis of amplified products from amplification reactions, such as multiplex PCR, can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label.

The methods and compositions provided herein provide increased sensitivity for detection of a mutated nucleic acid. Preferably the methods can detect mutated nucleic acid that is present in 10% or less, 1% or less, 0.1% or less, 0.01% or less, 0.001% or less, 0.0005% or less, 0.0003% or less, or 0.0002% or less than the total nucleic acid of a sample.

Various other cancer biomarkers suitable for detection using the methods and compositions provided herein include, but are not limited to, breast cancer markers, such as, GSTP1, RASSF1A (both described in Papadopoulou, E. et al., 1075 Ann. N.Y. Acad. Sci. 235-243 (2006); and RASSF1A (Papadopoulou, E., et al., and Coyle, et al., 16(2) Cancer Epidemiol. Biomarkers Prev. 192-196 (2007)), ATM (Papadopoulou, E., et al.), APC (Coyle, et al.), RARbeta2 (Hogue, M O, et al., 24(26) J. Clin. Oncol. 4262-4269, Epub 2006 Aug. 14 (2006)), and TP53 (Silva, J. M., et al., 8(12) Clin. Cancer Res. 3761-3766 (2002)); ovarian cancer markers, such as p53 (Swisher, E. M., et al., 193(3) American Journal of Obstetrics and Gynecology 662-667 (2005)); hepatocellular carcinoma markers, such as, p53 mutations (Huang, X. H., et al., 9(4) World J Gastroenterol. 692-695 (2003)), and p 16 (Le Roux, E., 53(3) Rev. Epidemiol. Sante Publique. 257-266 (2005)); and pancreatic cancer markers, such as K-ras (Castells, A., et al., 17(2) J. Clin. Oncol. 578-584 (1999)).

Oligonucleotides or combinations of oligonucleotides that are useful as primers or probes in the methods are also provided. These oligonucleotides are provided as substantially purified material.

Kits comprising oligonucleotides which may be primers for performing amplifications as described herein also are provided. Kits may further include oligonucleotides that may be used as probes to detect amplified nucleic acid. Kits may also include restriction enzymes for digesting non-target nucleic acid to increase detection of target nucleic acid by the oligonucleotide primers.

As used herein, the term "junction" refers to the position where target and non-target sequences are adjacent to one another due to a sequence change. For example, in the event of a translocation between sequence 1, ATGC and sequence 2, CGTA, the resulting mutated sequence or fusion sequence would be ATGCCGTA. The junction in this translocation example would be "CC." For example, in the even of an insertion of sequence 3, CCCC into sequence 4, ATGC, the resulting mutated sequence would be ATCCCCGC. The junctions in this event would be "TC" and "CG."

"Fragmentation" as used herein refers a process in which longer lengths of nucleic acid are broken up into shorter lengths of nucleic acid. Nucleic acids may be broken up or fragmented by chemical or biochemical means, preferably nucleic acids are fragmented in a manner that is reproducible, preferably nucleic acids are fragmented by one or more restriction endonucleases. The length of a fragment containing the nucleic acid segment of interest can depend on the length of the nucleic acid segment of interest as well as the restriction enzyme chosen to fragment the DNA.

A "restriction endonuclease" or "restriction enzyme" as used herein refers to an enzyme that cuts double-stranded DNA at a specific sequence (i.e., the recognition sequence or site). The frequency with which a given restriction endonuclease cuts DNA depends on the length of the recognition site of the enzyme. For example, some enzymes recognize sites that are four nucleotides long (referred to as "four cutters"). In general one can estimate how frequently an enzyme should cut a piece of DNA based the length of the recognition site and the assumption that the probability of any one nucleotide occurring at a given location is $1/4$. In the case of a "four cutter" a specific sequence of four nucleotides must be present. Assuming that each nucleotide has an equal chance (i.e., $1/4$) of occurring at any particular site within the four nucleotide sequence, then a four-cutter should on average cut once every 256 base pairs (i.e., $1/4 \times 1/4 \times 1/4 \times 1/4 = 1/256$). A similar calculation can be applied to any restriction enzyme as long as the length of its recognition site is known, making it possible to predict the size and number of a DNA fragments that would be obtained by cutting a DNA molecule of known size. This allows one of skill in the art to produce DNA fragments of known size. Restriction endonucleases are obtained from bacteria or are produced through recombinant technology and are readily available through numerous commercial sources.

As used herein, the term "increased detection" refers to the ability to detect lower amounts of target nucleic acid in the presence of non-target nucleic acid. For example, as non-target nucleic acid increases, fragmentation of the non-target nucleic acid increases the ability to detect a smaller fraction of target nucleic acid in total nucleic acid.

As used herein, the term "sample" or "test sample" refers to any liquid or solid (or both) material can be used to test for the presence of nucleic acids. In preferred embodiments, a test sample is obtained from a biological source (i.e., a "biological sample"), such as cells in culture or tissue cells from an animal, preferably, a human. Preferred sample sources include, but are not limited to, sputum (processed or unprocessed), bronchial alveolar lavage (BAL), bronchial wash (BW), blood, bone marrow, bodily fluids, cerebrospinal fluid (CSF), urine, plasma, serum or tissue (e.g., biopsy material). A body fluid sample refers to fluid containing samples from an individual including sputum (processed or unprocessed), bronchial alveolar lavage (BAL), bronchial wash (BW), blood, plasma, serum, and cerebrospinal fluid (CSF). The term "patient sample" as used herein refers to a sample obtained from a human seeking diagnosis and/or treatment of a disease.

As used herein, the term "oligonucleotide" refers to a short polymer composed of deoxyribonucleotides, ribonucleotides or any combination thereof. Oligonucleotides are generally between about 10, 11, 12, 13, 14 or 15 to about 150 nucleotides (nt) in length, more preferably about 10, 11, 12, 13, 14 or 15 to about 150 nt, more preferably about 10, 11, 12, 13, 14, or 15 to about 70 nt, and most preferably between about 20 to about 26 nt in length. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid sequence, while "specificity" is the probability that a test is negative, given that the person does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein, the term "substantially purified" in reference to oligonucleotides does not require absolute purity.

Instead, it represents an indication that the specified oligonucleotide is relatively more pure than it is in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well know in the art.

As used herein, the term "hybridize" or "specifically hybridize" refers to a process where two complementary nucleic acid strands anneal to each other under appropriately stringent conditions. Hybridizations are typically and preferably conducted with oligonucleotides Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The terms "target nucleic acid" or "target sequence" as used herein refer to a sequence which includes an allele or mutation of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequences, a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom.

"Genomic nucleic acid" or "genomic DNA" refers to some or all of the DNA from a chromosome. Genomic DNA may be intact or fragmented (e.g., digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

The term "flanking" as used herein means that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences can comprise a contiguous sequence of bases that do not hybridize to a target sequence, positioned 3' or 5' to a contiguous sequence of bases that hybridize under stringent hybridization conditions to a target sequence.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced from there.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-6, 858, 860 passim; Zhong, et al., Biotechniques 2001 April; 30(4): 852-6, 858, 860.

The term "multiplex PCR" as used herein refers to simultaneous amplification of two or more products which are each primed using a distinct primer pair.

As used herein, a "primer" for amplification is an oligonucleotide that specifically anneals to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, sequences that have "high sequence identity" have identical nucleotides at least at about 50% of aligned nucleotide positions, preferably at least at about 58% of aligned nucleotide positions, and more preferably at least at about 76% of aligned nucleotide positions.

As used herein "TaqMan® PCR detection system" refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, "about" means plus or minus 10%.

BRIEF DESCRIPTION OF THE FIGURES

FIG. 2A. Nucleotide sequence of a portion of the sequence coding for the wild-type form of the EGFR (SEQ ID NO:22). The two segments of highlighted unbolded text together represent the sequence for a forward mutation specific PCR primer (SEQ ID NO:1) specific for the E746_A750del mutant EGFR gene. Only a portion of the forward mutation specific primer is complementary to a contiguous segment of the wild-type EGFR gene. Highlighted bolded text indicates sequence for a reverse PCR primer (SEQ ID NO:2). The 15 bp region that is deleted is located between the two portions of the forward primer in the E746_A750del mutant EGFR gene. Boxed TTAA regions indicate MseI restriction sites.

FIG. 2B. Nucleotide sequence of a portion of the coding region of the E746_A750del mutant of EGFR (SEQ ID NO:23. Highlighted unbolded text indicates sequence of a forward mutation specific PCR primer (SEQ ID NO:1) specific for the E746_A750del mutant EGFR gene. Highlighted bolded text indicates sequence for a reverse PCR primer (SEQ ID NO:2). Boxed TTAA regions indicate MseI restriction sites.

FIG. 4. Nucleotide sequence of a portion of APC gene showing the exon 16 insertion sequence in unbolded text (SEQ ID NO:24). Highlighted bolded text indicates the sequence for a forward PCR primer (SEQ ID NO:3) and highlighted unbolded text indicates the sequence of a reverse PCR primer (SEQ ID NO:4). Boxed GAGG and CCTC regions indicate MnlI restriction sites.

FIG. 6. Nucleotide sequence of a portion of APC gene showing the exon 16 insertion sequence in unbolded text (SEQ ID NO:25). Highlighted bolded text indicates the sequence for a forward PCR primer (SEQ ID NO:5). Highlighted unbolded text indicates the sequence of a reverse PCR primer (SEQ ID NO:6). Boxed GAGG and CCTC regions indicate MnlI restriction sites.

FIG. 8. Nucleotide sequences of portions of wild-type (SEQ ID NO:28) and mutant EGFR genes (SEQ ID NO:29). Highlighted unbolded text indicates the sequence for a forward mutation specific PCR primer (SEQ ID NO:7) specific for the L858R mutant EGFR gene. Only a portion of the forward mutation specific primer is complementary to a contiguous segment of the wild-type EGFR gene. Highlighted bolded text indicates the sequence for a reverse PCR primer (SEQ ID NO:8). The bolded boxed base pair "T" indicates where the point mutation occurs in the L858R mutant EGFR gene. The bolded "G" in the forward mutation specific primer is the location of the locked nucleic acid. Highlighted unbolded text in the wild-type EGFR gene sequence indicates where the forward mutation specific primer would hybridize, or base pair. Boxed TTAA regions indicate MseI restriction sites. Boxed YGGCCR region, where Y=C or T; and R=A or G, indicates an EaeI restriction site.

FIG. 10. Nucleotide sequences of portions of wild-type TMPRSS2 (SEQ ID NO:30) and ERG (SEQ ID NO:31) and mutant fusion (SEQ ID NO:32) gene, TMPRSS2:ERG. Highlighted bolded text indicates the sequence for a forward mutation specific PCR primer (SEQ ID NO:9). Highlighted unbolded text indicates the sequence for a reverse mutation specific PCR primer (SEQ ID NO:10). Underlined regions in the wild-type sequences correspond to the depicted portion of the resulting fusion gene. Boxed CATG regions indicate FatI restriction sites.

FIG. 12. Nucleotide sequences of portions of wild-type TMPRSS2 (SEQ ID NO:33) and ETVI (SEQ ID NO:34) and mutant fusion (SEQ ID NO:35) gene, TMPRSS2:ETV1. Highlighted bolded text indicates sequence for a forward mutation specific PCR primer (SEQ ID NO:11). Highlighted unbolded text indicates sequence for a reverse mutation specific PCR primer (SEQ ID NO:12). Underlined regions in the wild-type sequences correspond to the depicted portion of the resulting fusion gene. Boxed CATG and TGCA regions indicate HpyCH4V restriction sites.

DETAILED DESCRIPTION OF THE INVENTION

Figure 1:
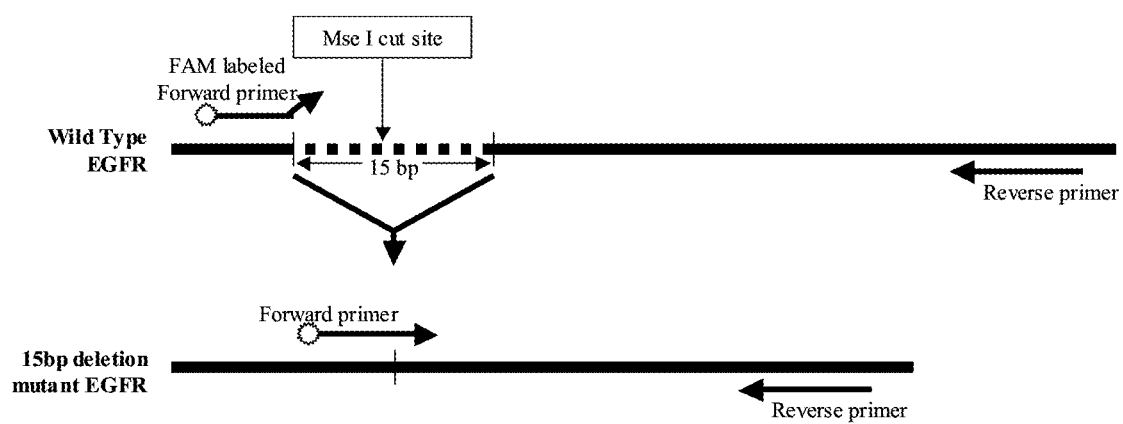
FIG. 1. Schematic diagram of primer placement for mutant specific PCR of a deletion mutation exemplified by E746_A750del in the EGFR gene. The deleted sequence is shown as a dashed line in the EGFR wild-type DNA. Horizontal arrows indicate primer placement for forward and reverse primers.

In accordance with the present invention, there are provided methods for determining whether a sample contains target nucleic acid. The methods outlined for detection of specific deletion mutations, insertion mutations, point mutations and translocation mutations can be applied to any biomarker in proximity to a restriction digestion recognition site, preferably a restriction digestion recognition site is disrupted by one or more mutations. A blueprint of the primer designs is depicted below but primer sequences will vary to fit the mutation to be detected. Restriction enzyme digestion sites will also depend on the sequence of the non-target sequence as compared to the target nucleic acid or fusion transcript but can follow the formats below. The frequency of various restriction sites found in DNA virtually ensures that a site unique to the non-target DNA of interest can be found for any target detection assay, thus these methodologies are applicable to a wide array of cancer biomarkers.

Primers

For the methods provided herein, a single primer could be used for detection, for example as in single nucleotide primer extension, or a second primer can be used which can be upstream or downstream of the mutation specific primer. One or more of the primers used may be mutation specific primers. Preferably, the mutation specific primer contains wild-type sequence, more preferably at least about 3-40 consecutive nucleotides of wild-type sequence.

Fragmentation

Fragmentation is preferably achieved by restriction enzyme treatment or one of other methods of fragmentation well known in the art. In order to reduce the likelihood of mis-priming or inability of the decreased ability for the primer to find a low copy target sequence among non-target sequences, a restriction enzyme recognition site is preferably present in the deleted sequence. Restriction digestion treatment prior to amplification will then cleave non-target sequences. Preferably, the mutation destroys a restriction enzyme recognition site such that the wild-type sequence will be digested, but the mutant sequence no longer contains the recognition site.

One of skill in the art would recognize that a restriction enzyme fragmentation method can be modified by using a restriction enzyme that cuts at a particular frequency or a particular site, or by using multiple restriction enzymes. The choice of enzyme or enzyme combinations is chosen to suit the target of interest in an assay. Enzymes for fragmentation can be chosen by using a restriction enzyme map of the region of interest. Such maps can be readily generated by software programs well-known to those of skill in the art.

Chemical fragmentation may include degradation by a nuclease such as DNase or RNase which generate fragments having 3'-OH, 5'-OH, 3'-phosphate and 5'-phosphate ends; depurination or depyrimidation with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations (see, for example, U.S. Pat. No. 6,495,320). It is possible to depurinate or depyrimidate the DNA, which is then fragmented in the presence of a base (i.e., "β-elimination") DNA can be fragmented by oxidation, alkylation or free radical addition mechanisms. Metal cations, which are often combined with organic molecules which may function as chemical catalysts, for example imidazole, are used for fragmenting RNA. This fragmentation is preferably carried out in an alkaline medium and generates fragments having 3'-phosphate ends. Chemical catalysts that may be used for nucleic acid fragmentation include MOPS, HEPES, PIPES, and bioorganic polyamines, such as spermine, spermidine and putrescine (Bibille et al., 27 Nucleic Acids Res. 3931-3937 (1999)).

Different nucleic acid fragmentation techniques have been described, for example, in Trawick et al., 98 Chem Rev. 939-960 (1998), Oivanen at al., 1998, 98 Chem Rev. 961-990 (1998) and Laayoon, et al. U.S. Pat. No. 6,902,891. A method for fragmenting and labeling RNA is described in WO88/04300A1, in which fragmentation is carried out using RNA which possesses enzymatic properties (ribozymes).

Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3rd Ed. Cold Spring Harbor Laboratory Press, Cold Spring Harbor, N.Y. (2001).

Preferential cleavage can be achieved my other methods known in the art such as the Maxam-Gilbert method. This method involves degrading DNA at a specific base using chemical reagents. A. M. Maxim et al., 65(1) Meth. in Enzym. 499-560 (1980). In general, this method starts with end labeled DNA and cleaves by base specific reagents. For example with guanine bases (the same principle applies to all four bases), DNA of interest is end-labeled (can be 5'- or 3'-end labeling). Then one kind of base is modified, for example with dimethyl sulfate (DMS) to methylate guanines. Conditions can be adjusted to achieve various frequencies of methylation. Following methylation. a reagent such as piperidine is added which causes loss of a methylated base and then breaks the DNA backbone at the site of the lost base (the apurinic site).

Deletion Mutations

In one approach, a mutation specific primer is designed for detecting a deletion mutation. Mutation specific primer can be designed to span the deleted region such that the primer contains wild-type sequence that lies 5' and 3' of the deleted region or the complement thereof. Thus, the mutation specific primer cannot bind to the wild-type sequence and cannot produce an amplicon.

Oligonucleotide primers may be designed for amplifying regions of mutated nucleic acid. In one approach, a primer pair is designed for detecting a deletion mutation. In one embodiment, the primer pair is designed to hybridize to a specified segment of the EGFR gene. The sequence of exemplary oligo primers are shown as highlighted regions in FIGS. 2A and 2B (SEQ ID NOs:1 and 2). Exemplary primer pairs for amplifying a region of the EGFR sequence for the E746_A750del mutation use a forward primer (mutation specific primer) with SEQ ID NO:1 (5'-CCCGTCGCTAT-CAAAACATC-3') and a reverse primer with SEQ ID NO:2 (5'-ATGTGGAGATGAGCAGGGTCT-3'). In this example, the mutation specific primer spans sequence that is deleted in the mutated sequence. Thus, the primer cannot anneal to the wild-type sequence due to the presence of the 15 base pairs. Preferably, the primers with SEQ ID NOs:1 and 2 are each or both used in conjunction with a restriction enzyme digestion treatment with MseI which has a recognition site of TTAA. The mutation specific primer in that example lies 5' and 3' of the 15 bp deleted region, it cannot bind to the wild-type sequence, thus making the primer mutation specific for the deletion mutation. FIGS. 1 and 2 illustrate this example of detecting the E746_A750del mutation in the EGFR gene.

Insertion Mutations

In one approach, a mutation specific primer is designed for detecting an insertion mutation. A mutation specific primer can be designed to span all or a portion of the inserted region such that the primer includes all or a part of the inserted region. A primer could be designed to span the either or both junctions of the inserted sequence, for example, the primer sequence would include a portion of wild-type sequence that is adjacent to the inserted sequence or the complement thereof. Thus, the mutation specific primer is not complementary to the wild-type sequence and cannot produce an amplicon.

Preferably, the insertion destroys a restriction enzyme recognition site such that the wild-type sequence will be digested, but the mutant sequence no longer contains the recognition site. Restriction digestion treatment prior to amplification will then cleave non-target sequences. Restriction digestion can also enhance sensitivity by cleaving away sequence surrounding target nucleic acid and facilitate amplification.

In one embodiment, a primer pair is designed to detect the 758 base pair insertion in exon 16 insertion in the APC gene. The sequence of exemplary oligo primers are shown as highlighted regions in FIG. 4 (SEQ ID NOs:3 and 4). Exemplary primer pairs for amplifying a region of the APC sequence for an exon 16 (Miki, et al., 52(3) Cancer Research 643-645 (1992)) insertion mutation use a forward primer (mutation specific primer) with SEQ ID NO:3 (5'-CTTC-CACAATGGTTGAACTAG-3') and a reverse primer (mutation specific primer) with SEQ ID NO:4 (5'-CATC-CATGTCCCTACAAAGG-3'). In this example, both forward and reverse primers are mutation specific because they lie within the insertion sequence. Preferably, the primers with SEQ ID NOs:3 and 4 are each or both used in conjunction with a restriction enzyme digestion treatment with MnlI which has a recognition site of CCTC.

Figure 3:
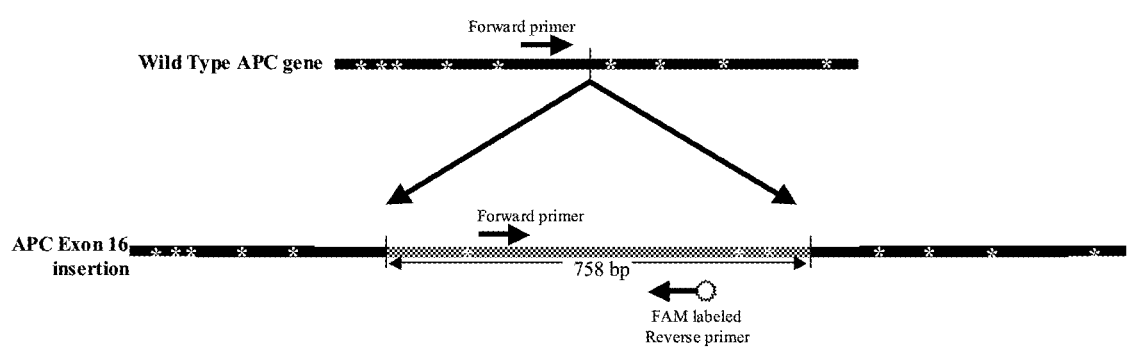
FIG. 3. Schematic diagram of primer placement for mutant specific PCR of an insertion mutation exemplified by the exon 16 mutation in the APC gene. Horizontal arrows indicate primer placement for forward and reverse primers. The gray region represents the inserted sequence. White stars indicate MnlI restriction sites.

The mutation specific primer in that example lies within the inserted region. Because the primers lie within the insertion sequence, no amplification will occur unless the insertion is present. In addition, there are MnlI restriction sites upstream and downstream of the desired amplification product which will facilitate amplification subsequent to digestion by removing surrounding sequence. FIGS. 3 and 4 illustrate this example of detecting the exon 16 insertion mutation in the APC gene.

In another embodiment, a primer pair is designed to detect the 758 base pair insertion in exon 16 insertion in the APC gene. The sequence of exemplary oligo primers are shown as highlighted regions in FIG. 6 (SEQ ID NOs:5 and 6). Exemplary primer pairs for amplifying a region of the APC sequence for an exon 16 insertion mutation use a forward primer (mutation specific primer) with SEQ ID NO:5 (5'-GAGCCATTTATACAGAAAGATG-3') and a reverse primer (mutation specific primer) with SEQ ID NO:6 (5'-GAAATACCATTTGACCCAGC-3'). In this example, the forward primer lies outside the insertion sequence and reverse primer lies inside the insertion sequence. Both are mutation specific because an amplicon will not be produced in the absence of the insertion sequence. Preferably, the primers with SEQ ID NOs:5 and 6 are each or both used in conjunction with a restriction enzyme digestion treatment with MnlI which has a recognition site of CCTC.

Figure 5:
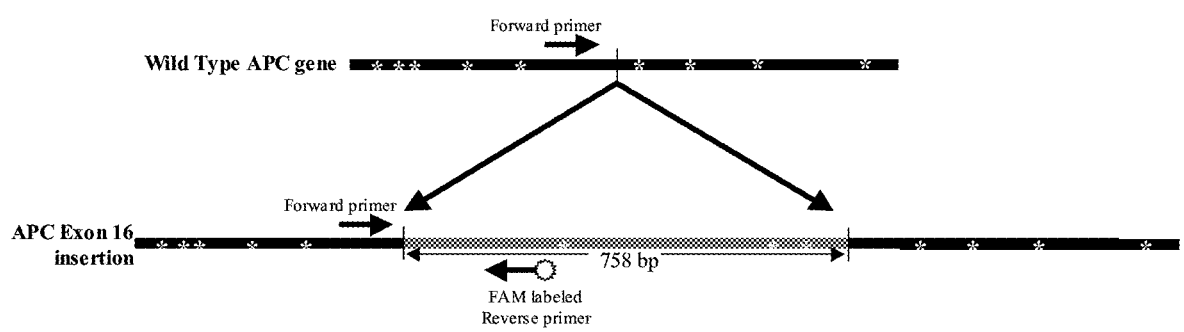
FIG. 5. Schematic diagram of alternative primer placement for mutant specific PCR of an insertion mutation exemplified by the exon 16 mutation in the APC gene. Horizontal arrows indicate primer placement for forward and reverse primers. The gray region represents the inserted sequence. White stars indicate MnlI restriction sites.

One primer is upstream of the insertion site and the second is within the insertion sequence. In addition, there are MnlI restriction sites less than 20 bases upstream and downstream of the desired amplification product which will facilitate amplification of the target nucleic acid by removing surrounding sequence. The wild-type APC sequence is heavily targeted by MnlI restriction enzyme with a number of sites immediately downstream of the forward primer. The insertion sequence in the APC exon 16 insertion mutant contains a region devoid of MnlI restriction sites that is used as the template for PCR. Digestion with MnlI prior to PCR eliminates any linear amplification that may occur by forward primer binding to the wild type APC gene. Fluorescent PCR can be performed using one forward primer that binds to the APC gene just before the insertion and one insertion specific reverse primer (unlabeled forward, FAM labeled reverse) designed to specifically recognize the insertion sequence in the region not containing MnlI restriction sites. FIGS. 5 and 6 illustrate this example of detecting the exon 16 insertion mutation in the APC gene.

Substitution Mutations

In one approach, a mutation specific primer is designed for detecting one or more substitution mutations. A mutation specific primer can be designed to include one or more substitutions. In a preferred embodiment, the 3' nucleotide of the primer can be designed such that it contains the mutated base pair and does not bind, hybridize, or base pair, in the wild-type gene and thus cannot elongate. In another preferred embodiment, the mutated base pair is located at the −1 position at the 3'-end of a mutation specific primer (i.e., the penultimate base).

Preferably, the one or more substitutions destroys a restriction enzyme recognition site such that the wild-type sequence will be digested, but the mutant sequence no longer contains the recognition site. Restriction digestion treatment prior to amplification will then cleave non-target sequences.

In further preferred embodiments, the mutated base pair in the mutation specific primer is a locked nucleic acid (LNA). The locked nucleic acid provides increased specificity by increasing the melting temperature of the of a primer containing the substitution base. This allows for the use of an increased annealing temperature during amplification which decreases amplification of wild type sequences.

In one embodiment, a primer pair is designed to detect the L858R mutation in the EGFR gene. The sequence of exemplary oligo primers are shown as highlighted regions in FIG. 8 (SEQ ID NOs:7 and 8). Exemplary primer pairs for amplifying a region of the EGFR sequence for the L858R mutation use a forward primer (mutation specific primer) with SEQ ID NO:7 (5'-TCACAGATTTTGGGCGG-3') and a reverse primer with SEQ ID NO:8 (5'-CCTGGTGTCAG-GAAAATGCT-3'). In this example, the mutation specific primer contains the mutated sequence at the terminal base. Thus, it will not properly anneal to the wild-type sequence because the last base is not complementary. Preferably, the primers with SEQ ID NOs:7 and 8 are each or both used in conjunction with a restriction enzyme digestion treatment with EaeI which has a recognition site of YGGCCR, where Y=C or T and R=A or G. As shown in FIG. 8, the boxed MseI restriction sites, TTAA, illustrate that a simultaneous reaction, such as a multiplex PCR reaction, can be used to detect either or both the E746_A750del and L858R mutations in the same reaction. Digestion with both MseI and EaeI does not disrupt the L858R sequence of interest.

Figure 7:
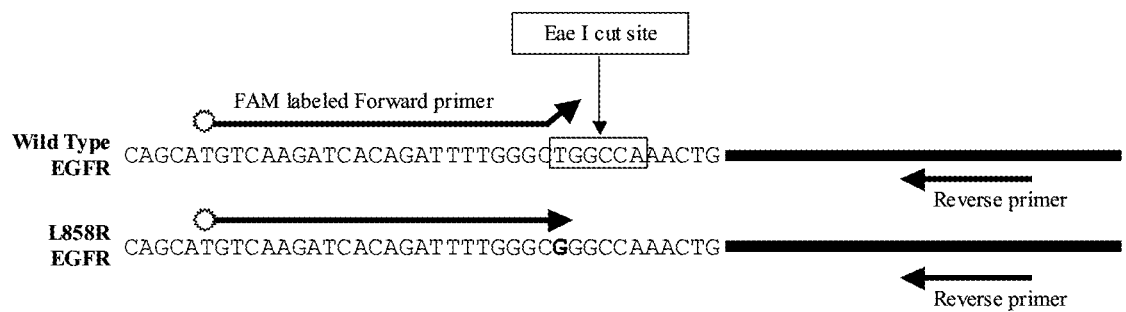
FIG. 7. Schematic diagram of primer placement for mutant specific PCR of a substitution mutation exemplified by point mutation L858R in the EGFR gene. Horizontal arrows indicate primer placement for forward and reverse primers. The boxed sequence indicates the EaeI restriction site. The bolded "G" base pair represents the substituted base (SEQ ID NO:26 and SEQ ID NO:27, respectively in order of appearance).

The mutation specific primer in that example includes the mutated base pair sequence, a G, at its 3' end. Because the primer is not complementary to the wild-type sequence, which contains a T, elongation will not occur. The EaeI cut site allows cleavage of the wild-type EGFR gene but is destroyed by the T-*G conversion. Thus, when the L858R EGFR mutant is present, the recognition site is no longer present and can no longer be digested by EaeI. FIGS. 7 and 8 illustrate this example of detecting the L858R mutation in the EGFR gene.

Translocation Mutations

In one approach, a mutation specific primer is designed for detecting one or more translocation mutations. A mutation specific primer can be designed to span the junction of the translocation or the complement thereof. A primer pair could be designed to so that one primer is upstream of the translocation junction and the second is downstream of the junction. Thus, when the primer pair is used on wild-type sequence, no amplification products will be produced because the locations of the primers relative to each other cannot be amplified. However, when the translocation is present, the primers are in close enough proximity of each other such that an amplification product can be produced. For example, the primer can be designed to include a portion of the first gene and a portion of the second gene, where the genes are located on different chromosomes in wild-type form but are adjacent to one another in the mutated form.

Preferably, one or more translocations destroys a restriction enzyme recognition site such that the wild-type sequence will be digested, but the mutant sequence no longer contains the recognition site. Restriction digestion treatment prior to amplification will then cleave non-target sequences.

In one embodiment, a primer pair is designed to detect the TMPRSS2:ERG or translocation mutation of the TMPRSS2 and ERG genes. The sequence of exemplary oligo primers are shown as higlighted regions in FIG. 10 (SEQ ID NOs:9 and 10). Exemplary primer pairs for amplifying a region of the TMPRSS2 and ERG sequences for the TMPRSS2:ERG translocation mutation use a forward primer (mutation specific primer) with SEQ ID NO:9 (5'-CGAGCTAAGCAG-GAGGCGG-3') and a reverse primer (mutation specific primer) with SEQ ID NO:10 (5'-GTCCATAGTCGCTG-GAGGAG-3'). In this example, while both primers anneal to wild-type sequences, they are mutation specific when used in conjunction with each other because they will not produce an amplification product unless the translocation is present in the nucleic acid sample. Preferably, the primers with SEQ ID NOs:9 and 10 are each or both used in conjunction with a restriction enzyme digestion treatment with FatI which has a recognition site of CATG.

In another embodiment, a primer pair is designed to detect the TMPRSS2:ETV1 translocation mutations of the TMPRSS2 and ETV1 genes. The sequence of exemplary oligo primers are shown as highlighted regions in FIG. 12 (SEQ ID NOs:11 and 12). Exemplary primer pairs for amplifying a region of the TMPRSS2 and ERG sequences for the TMPRSS2:ETV1 translocation mutation use a forward primer (mutation specific primer) with SEQ ID NO:11 (5'-CGAGCTAAGCAGGAGGCGG-3') and a reverse primer (mutation specific primer) with SEQ ID NO:12 (5'-ACTTTCAGCCTGATAGTCTGG-3'). In this example, while both primers anneal to wild-type sequences, they are mutation specific when used in conjunction with each other because they will not produce an amplification product unless the translocation is present in the nucleic acid sample. Preferably, the primers with SEQ ID NOs:11 and 12 are each or both used in conjunction with a restriction enzyme digestion treatment with HpyCH4VI which has a recognition site of TGCA.

Figure 9:
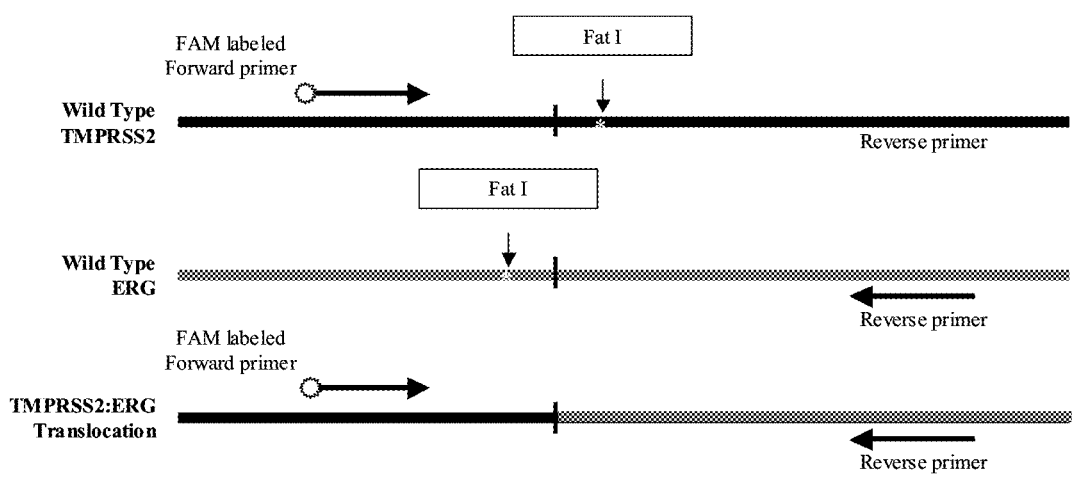
FIG. 9. Schematic diagram of primer placement for mutant specific PCR of a translocation mutation exemplified by the TMPRSS2:ERG fusion transcript. Horizontal arrows indicate primer placement for forward and reverse primers. White stars indicate FatI restriction sites.
Figure 11:
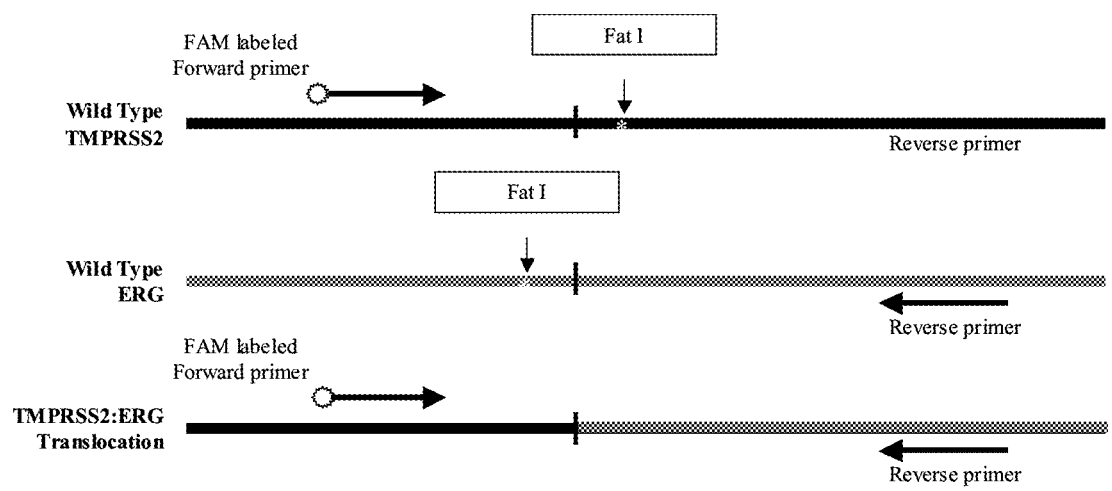
FIG. 11. Schematic diagram of primer placement for mutant specific PCR of a translocation mutation exemplified by the TMPRSS2:ETV1 fusion transcript. Horizontal arrows indicate primer placement for forward and reverse primers. White stars indicate FatI and HpyCH4V restriction sites.
Figure 13:
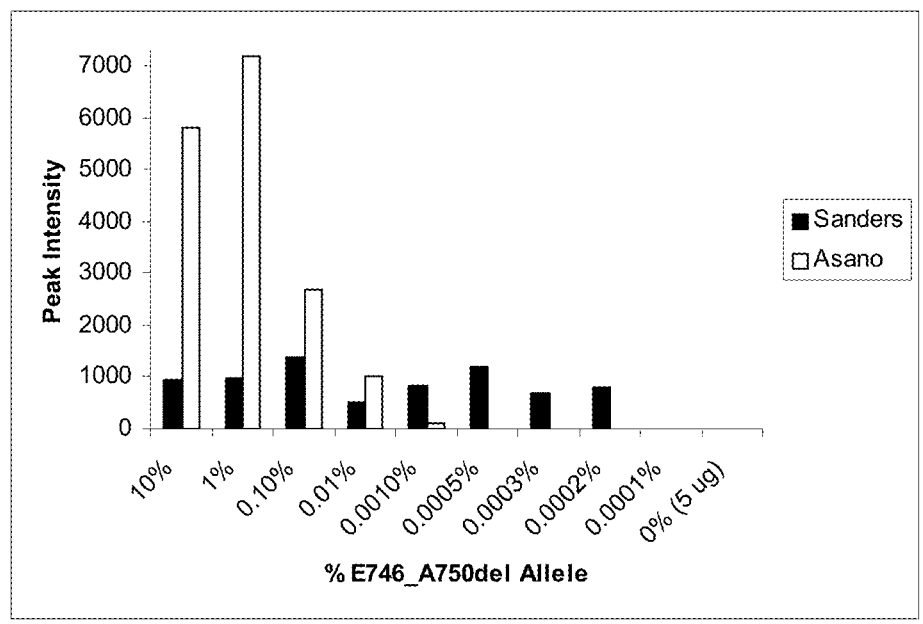
FIG. 13. Graphical depiction of results of sensitivity comparison assay between Sanders method and Asano method for detection of the E746_A750del mutation in EGFR.

In these embodiments, the Fat I and HpyCH4V cut sites allow cleavage of the wild-type TMPRSS2, ERG, and ETV1 in the regions that are absent in the fusion transcripts, essentially "decontaminating" the sample of wild-type TMPRSS2 and ERG or ETV1 translocations. Because the forward and reverse primer sequences are only both present in the fusion transcripts, only the nucleic acids representing a fusion transcript will yield PCR products. FIGS. 9 and 10 illustrate this example of detecting the TMPRSS2:ERG translocation mutation.

Sample Preparation

The method may be performed using any sample containing nucleic acid. Samples may be obtained by standard procedures and may be used immediately or stored (e.g., the sample may be frozen between about −15° C. to about −100° C.) for later use. Samples may be obtained from patients suspected of having a mutated nucleic acid sequence, for example from a tumor cell or cancer cells. The presence of mutated nucleic acids in a sample can be determined by amplifying cancer marker regions. Thus, any liquid or solid material believed to contain cancer marker nucleic acids can be an appropriate sample. Preferred sample tissues include plasma, blood, bone marrow, body fluids, cerebrospinal fluid, urine and others. Heparin is known to inhibit PCR (Beutler, et al. BioTechniques 9:166, 1990), so samples containing heparin are not ideal for the uses contemplated herein. Nucleic acid extraction techniques that remove heparin are known in the art. These techniques may be used to remove heparin from samples to make the samples more suitable for amplification.

The sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be genomic DNA, cDNA, single stranded DNA or mRNA.

Oligonucleotides

Oligonucleotide primers may be approximately 15-100 nucleotides in length. Of the specific oligonucleotides provided herein, additional variations of the primers comprise all or a portion of the SEQ IDs described herein. Other preferred oligonucleotide primers include an oligonucleotide sequence that hybridizes to the complement of a 15-100 nucleotide sequence that comprises the complement of all or a portion of the SEQ IDs described herein. Such oligonucleotides may be substantially purified.

Amplification of Nucleic Acids

Nucleic acid samples or isolated nucleic acids may be amplified by various methods known to the skilled artisan. Preferably, PCR is used to amplify mutated nucleic acids of interest. In this method, two or more oligonucleotide primers that flank or include, and anneal to opposite strands of a nucleic acid of interest are repetitively annealed to their complementary sequences, extended by a DNA polymerase (e.g., AmpliTaq Gold polymerase), and heat denatured, resulting in exponential amplification of the target nucleic acid sequences. Cycling parameters can be varied, depending on the length of nucleic acids to be extended. The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

Assay controls may be used in the assay for detecting a mutated nucleic acid sequence. An internal positive amplification control (IPC) can be included in the sample, utilizing oligonucleotide primers and/or probes.

Detection of Amplified Nucleic Acids

Amplification of nucleic acids can be detected by any of a number of methods well-known in the art such as gel electrophoresis, column chromatography, hybridization with a probe, or sequencing.

In one approach, sequences from two or more regions of interest are amplified in the same reaction vessel. In this case, the amplicon(s) could be detected by first size-separating the amplicons then detection of the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel, (a 2% to 3% agarose gel for about 150 to about 300 base pair amplicons) or a 6% to 10% polyacrylamide gel. The separated nucleic acids can then be stained with a dye such as ethidium bromide and the size of the resulting stained band or bands can be compared to a standard DNA ladder.

In another embodiment, two or more regions of interest are amplified in separate reaction vessels. If the amplification is specific, that is, one primer pair amplifies for one region of interest but not the other, detection of amplification is sufficient to distinguish between the two types—size separation would not be required.

In some embodiments, amplified nucleic acids are detected by hybridization with a mutation-specific probe. Probe oligonucleotides, complementary to a portion of the amplified target sequence may be used to detect amplified fragments. Amplified nucleic acids for each of the target sequences may be detected simultaneously (i.e., in the same reaction vessel) or individually (i.e., in separate reaction vessels). In preferred embodiments, the amplified DNA is detected simultaneously, using two distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., Cy5®, Cy3®, FITC, rhodamine, lanthamide phosphors, Texas red), 32P, 35S, 3H, 14C, 125I, 131I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

A probe oligonucleotide, complementary to the amplified region of nucleic acid, is used to detect the amplification of mutated nucleic acids. The probe may be detectably labeled by methods known in the art. The binding of a probe to the amplified region of the mutated nucleic acid may be determined by hybridization as is well known in the art. Hybridization may be detected in real time or in non-real time.

One general method for real time PCR uses fluorescent probes such as the TaqMan® probes, molecular beacons and scorpions. Real-time reverse-transcriptase (RT) PCR quantitates the initial amount of the template with more specificity, sensitivity and reproducibility, than other forms of quantitative reverse transcriptase PCR, which detect the amount of final amplified product. Real-time RT-PCR does not detect the size of the amplicon. The probes employed in TaqMan® and molecular beacon technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore).

Suitable fluorescent moieties include the following fluorophores known in the art:
4-acetamido-4'-isothiocyanatostilbene-2,2'disulfonic acid
acridine and derivatives:
   acridine
   acridine isothiocyanate
Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes)
5-(2'-aminoethy)aminonaphthalene-1-sulfonic acid (EDANS)
4-amino-N-[3-vinylsulfonyl)phenyl]naphthalimide-3,5 disulfonate (Lucifer Yellow VS)
N-(4-anilino-1-naphthyl)maleimide
anthranilamide
Black Hole Quencher™ (BHQ™) dyes (biosearch Technologies)
BODIPY® R-6G, BOPIPY® 530/550, BODIPY® FL
Brilliant Yellow
coumarin and derivatives:
   coumarin
   7-amino-4-methylcoumarin (AMC, Coumarin 120)
   7-amino-4-trifluoromethylcouluarin (Coumarin 151)
Cy2®, Cy3®, Cy3.5®, Cy5®, Cy5.5®
cyanosine
4',6-diaminidino-2-phenylindole (DAPI)
5', 5''-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
Eclipse™ (Epoch Biosciences Inc.)
eosin and derivatives:
   eosin
   eosin isothiocyanate
erythrosin and derivatives:
   erythrosin B
   erythrosin isothiocyanate
ethidium
fluorescein and derivatives:
   5-carboxyfluorescein (FAM)
   5-(4,6-dichlorotriazin-2-yl)aminofluorescein (DTAF)
   2',7'-dimethoxy-4'5'-dichloro-6-carboxyfluorescein (JOE)
   fluorescein
   fluorescein isothiocyanate (FITC)
   hexachloro-6-carboxyfluorescein (HEX)
   QFITC (XRITC)
   tetrachlorofluorescein (TET)
fluorescamine
IR144
IR1446
Malachite Green isothiocyanate
4-methylumbelliferone
ortho cresolphthalein
nitrotyrosine
pararosaniline
Phenol Red
B-phycoerythrin, R-phycoerythrin
o-phthaldialdehyde
Oregon Green®
propidium iodide
pyrene and derivatives:
   pyrene
   pyrene butyrate
   succinimidyl 1-pyrene butyrate
QSY® 7, QSY® 9, QSY® 21, QSY® 35 (Molecular Probes)
Reactive Red 4 (Cibacron® Brilliant Red 3B-A)
rhodamine and derivatives:
   6-carboxy-X-rhodamine (ROX)
   6-carboxyrhodamine (R6G)
   lissamine rhodamine B sulfonyl chloride
   rhodamine (Rhod)
   rhodamine B
   rhodamine 123
   rhodamine green
   rhodamine X isothiocyanate
   sulforhodamine B
   sulforhodamine 101 sulfonyl chloride derivative of sulforhodamine 101 (Texas Red)

N,N,N',N'-tetramethyl-6-carboxyrhodamine (TAMRA)

tetramethyl rhodamine tetramethyl rhodamine isothiocyanate (TRITC)

riboflavin rosolic acid terbium chelate derivatives

Other fluorescent nucleotide analogs can be used, see, e.g., Jameson, 278 Meth. Enzymol. 363-390 (1997); Zhu, 22 Nucl. Acids Res. 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, 9 Mol. Cell. Probes 145-156 (1995).

Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, e.g., Cy3® or Cy50 and then incorporated into genomic nucleic acids during nucleic acid synthesis or amplification. Nucleic acids can thereby be labeled when synthesized using Cy3®- or Cy5®-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu, 18 Nat. Biotechnol. 345-348 (2000).

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulphur containing side chains of amino acids. See, e.g., U.S. Pat. Nos. 5,580,990; 5,714,327; and 5,985,566; and European Patent No. 0539466.

The binding of a probe to the marker sequence flanking the tandem repeat region may be determined by hybridization as is well known in the art. Hybridization may be detected in real time or in non-real time.

TaqMan® probes (Heid, et al., 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

TaqMan® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A 'G' adjacent to the reporter dye quenches reporter fluorescence even after cleavage.

Other methods of probe hybridization detected in real time can be used for detecting amplification of mutated nucleic acids. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target sequence, the probe is unfolded, the quencher is moved from the fluorophore, and the resultant fluorescence can be detected.

Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC) and the like. Suitable quenchers include tetra-methylcarboxyrhodamine (TAMRA) 4-(4-dimethylaminophenylazo) benzoic acid ("DABCYL" or a DABCYL analog) and the like. Tetramethylrhodamine (TMR) or 5-carboxyrhodamine 6G (RHD) may be combined as donor fluorophores with DABCYL as quencher. Multiplex TaqMan® assays can be performed using multiple detectable labels each comprising a different donor and quencher combination. Probes for detecting amplified sequence in real time may be stored frozen (−10° to −30° C.) as 100 M stocks. TaqMan® probes are available from Applied BioSystems (4316032).

In a preferred embodiment, real time PCR is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan® probes specific for each allele are included in the PCR assay. These probes contain a reporter dye at the 5' end and a quencher dye at the 3' end. Each allele specific probe is conjugated with a different fluorescent reporter dye. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation.

Real Time detection on the ABI Prism 7900HT or 7900HT Sequence Detector monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

To minimize the potential for cross contamination, reagent and mastermix preparation, specimen processing and PCR setup, and amplification and detection are all carried out in physically separated areas. In addition, Uracil-N-Glycosylase is utilized (along with the incorporation of Uracil into PCR amplicons) to eliminate carry over contamination.

The following examples serve to illustrate the present invention. These examples are in no way intended to limit the scope of the invention.

Example 1

E746_A750 Deletion

Background:
Somatic mutations in the tyrosine kinase (TK) domain of the EGFR gene are associated with clinical response to TK inhibitors in patients with non-small cell lung cancer (NSCLC). An assay that detects such mutations in plasma provides a noninvasive procedure to assess suitability for TK inhibitor therapy. Described below are 1) the development of a sensitivity assay to detect the E746_A750 deletion (E746_A750del) in the TK domain of EGFR in plasma; and 2) optimization of the assay for plasma DNA extraction.

Methods:
The assay uses MseI to specifically digest wild-type (WT) genomic DNA (gDNA) to reduce non-specific amplification. After digestion, samples are PCR-amplified using one unlabeled primer and one FAM-labeled primer spanning the E746_A750 deletion region. The fluorescence signal is detected with an automated genetic analyzer. Serial dilution studies were conducted using H1650 gDNA, which is a E746_A750 deletion cell line) diluted in WT gDNA after MseI digestion. To assess detection of the deletion in plasma, 3-4 mL of whole blood was spiked with 1-37 ng H1650 gDNA; gDNA from the separated plasma was then extracted by silica column/2-propanol precipitation, digested with MseI, and amplified as above. Several extraction methods (silica column, magnetic bead, phenol:chloroform, and 2-propanol precipitation) were evaluated using pooled plasma samples and phosphate buffer solution (PBS) spiked with 10-350 ng of gDNA.

Results:
Using a combined approach of digesting the WT EGFR allele followed by deletion-specific fluorescent PCR, the equivalent of circa 1 copy of the E746_A750 deletion (10 pg gDNA) diluted to 0.001% could be detected. Furthermore, the E746_A750 deletion was successfully detected in ⅕ the final DNA volume (5 µl) in all spiked blood samples. In the DNA extraction method evaluation, the magnetic bead-based method yielded the highest percent recovery of gDNA from PBS (69% recovery of the 10 ng sample). Phenol:chloroform extraction gave the highest yield with pooled plasma samples.

Conclusions:
The combination of an optimized DNA extraction method, clearing the plasma DNA sample of amplifiable WT DNA by restriction digestion, and mutation-specific fluorescent PCR provides a highly sensitive assay for detection of somatic mutations in plasma.

Example 2

Preparation of and Sensitivity Studies for Detection of EGFR Mutations

Serial dilution studies were conducted using H1650 gDNA (E746_A750 deletion mutation cell line) diluted in wild-type gDNA with no treatment of after MseI digestion. For each dilution, 10 pg of H1650 gDNA. H1650 is a heterozygous cell line, thus, 50% of the DNA contributes to the deletion allele and 50% to the wild-type allele) was spiked into wild-type gDNA at varying concentrations to yield 0.001%-10% of the exon 19 deletion in the background of wild-type allele. Nucleic acid is spiked into a sample in order to control the amount of target nucleic acid in a sample and test the sensitivity of the assay to detect various amounts, in particular low amounts, of target nucleic acid. The results show that peaks were detected corresponding to the deletion mutant at levels of 0.01% in non-treated samples and at least 0.001% when digested with MseI. These results are presented in Table 1.

TABLE 1

Exon 19 deletion tumor DNA spiked into purified DNA wild-type DNA

| % Exon 19 deletion allele | DNA Amount per reaction Concentration | | Peak Detected | |
|---|---|---|---|---|
| | Wild-Type | Exon 19 Deletion | No Treatment | MseI Treated |
| 10.00% | 45 pg | 10 pg (50% E746_A750del) | Yes | Yes |
| 1.000% | 495 pg | 10 pg (50% E746_A750del) | Yes | No |
| 0.100% | 5 ng | 10 pg (50% E746_A750del) | Yes | Yes |
| 0.010% | 50 ng | 10 pg (50% E746_A750del) | Yes | Yes |
| 0.001% | 500 ng | 10 pg (50% E746_A750del) | No | Yes |
| 0.000% | 500 ng | 0 pg | No | No |

*10 pg of tumor DNA was spiked into wild-type DNA at varying concentrations, but since 1 allele is wild-type, only half of the tumor DNA contributes to exon 19 deletion DNA and the other half to the wild-type allele To assess detection of the deletion in plasma, 3-4 mL whole blood was spiked with 1-37 ng H1650 gDNA; gDNA from the separated plasma was then extracted (QiaAmp DNA Blood Midi Kit), further concentrated by ethanol or isopropanol precipitation, and digested with MseI. The digested DNA was then subjected to fluorescent PCR using deletion-specific primers.

TABLE 2

Exon 19 deletion tumor DNA spiked into blood

| Precipitation Method | Amt of Spiked H1650 gDNA | Peak Detected No Treatment | Peak Detected Mse I Treated |
|---|---|---|---|
| Ethanol Precipitation | 37 ng | No | Yes |
|  | 1 ng | No | No |
| Isopropanol Precipitation | 37 ng | NT | Yes |
|  | 1 ng | NT | Yes |

*All samples were first extracted using the QiaAmp DNA Blood Midi kit, then further precipitated by ethanol or isopropanol precipitation
NT, Not tested

Example 3

Method Comparison of EGFR Mutation Detection

A method comparison was performed to demonstrate the sensitivity of the EGFR mutation detection assay disclosed herein (also referred to as the Sanders method) which is designed to be able to detect mutations in plasma from NSCLC patients. In this study, the method disclosed herein was compared with two other methods (Asano, 2006 and Ohnishi, 2006) that claim high sensitivity for detecting E746_A750del. The Asano and Ohnishi methods were performed as described in the respective publications but included a fluorescent label on the forward primer. Amplification products were then analyzed by capillary electrophoresis for fluorescent detection of the PCR fragments using an ABI 3100 Genetic Analyzer. Table 3 shows the expected and observed fragment sizes for each fragment.

TABLE 3

Expected and observed fragment sizes

| Method | Fragment | Expected Size | Observed Size |
|---|---|---|---|
| Sanders | Wild-Type EGFR | 197 | 194 |
|  | E746_A750del | 153 | 151 |
| Asano | Wild-Type EGFR | 138 | 135 |
|  | E746_A750del | 123 | 120 |
| Ohnishi | E746_A750del | 133 | 138 |

*Due to the mobility shift of PCR primer/products fluorescently labeled with FAM, some of the amplicons are slightly shifted from the expected size in the ABI 3100 Genetic Analyzer.

The assay disclosed herein has been previously detected as little as 10 pg of H1650 cell line DNA (circa 1 copy of the E746_A750del mutation) at as low as 0.001% in the background of the wild-type EGFR gene. Therefore, all three methods (Sanders, Asano and Ohnishi) were tested for their ability to detect 10 pg of H1650 cell line DNA at levels ranging from 0.0005% to 10% in the background of the wild-type EGFR gene (Table 4).

TABLE 4

Sensitivity of Sanders, Asano, and Ohnishi methods for detecting the E746_A750del mutation.

| | Sanders Method | | Asano Method | | Ohnishi Method |
|---|---|---|---|---|---|
| % H1650 DNA | Deletion Peak Intensity | Wild-Type Peak Intensity (1/5) | Deletion Peak Intensity (120 bp)* | Wild-Type Peak Intensity (135 bp)* | Deletion Peak Intensity (138 bp)* |
| 10% | 937 | 0 | 5811 | 0 | 0 |
| 1% | 989 | 166 | 7209 | 195 | 0 |
| 0.10% | 1395 | 152 | 2685 | 1746 | 0 |
| 0.01% | 520 | 1395 | 1004 | 3682 | 0 |
| 0.001% | 820 | 796 | 97 | 7087 | 0 |
| 0.0005% | 1184 | 2321 | 0 | 7338 | 167 |
| 0.0003% | 699 | 3942 | NT | NT | NT |
| 0.0002% | 803 | 3324 | NT | NT | NT |
| 0.0001% | 0 | 3798 | 0 | 4603 | NT |
| 0% (5 µg) | 0 | 2287 | 0 | 3836 | NT |
| 0% (50 ng) | 0 | 0 | 0 | 5280 | 0 |

*Sizes indicated are the actual size
NT = Not Tested

The results of this comparison indicate that the Sanders method detects circa 1 copy of the E746_A750del mutation in as little as 0.0005% in the background of the wild-type EGFR gene. (6.6 picograms (pg) is equivalent to one copy, so 10 pg is 1.5 copies, thus, circa is used to indicate the approximate copy number.) The Asano method demonstrated strong peaks at 0.01-10% levels and a weak peak at 0.001%, but no detectable amplification at 0.0005%. The Ohnishi method was unable to detect circa 1 copy of the E746_A750del mutation as determined by the absence of any peak from 0.001%-10% levels. However, a weak peak was observed in the 0.0005% sample, although this is most likely attributed to background amplification of the wild-type EGFR gene due to the very high levels of wild-type DNA present in the sample.

The Asano and Ohnishi methods were also tested for their ability to detect the E746_A750del mutation at high and low copy numbers without interfering wild-type DNA spike into the sample. Table 5 shows that the Asano method was successful at detecting both a high copy numbers (850 pg=130 copies) and low copy numbers (10 pg=~1 copy) of the mutation, as also demonstrated above. However, while the Ohnishi method successfully detected high copy numbers of the mutation, it failed at detecting low copy numbers.

TABLE 5

Detection of low and high copy numbers of the E746_A750del mutation.

| | Asano Method | | Ohnishi Method |
|---|---|---|---|
| H1650 DNA (pg/rxn) | Deletion Peak Intensity (120 bp)* | Wild Type Peak Intensity (135 bp)* | Deletion Peak Intensity (138 bp)* |
| 850 | 7345 | 0 | 2008 |
| 10 | 2422 | 0 | 0 |

*Sizes indicated are the actual size

The results presented in this study confirm that the Sanders assay for detection of the exon 19 EGFR deletion (E746_A750del) utilizing restriction digestion followed by deletion specific fluorescent PCR, demonstrates superior sensitivity over methods in the prior art, in particular, the methods described by Asano and Ohnishi.

Example 4

Detection of E746_A750del Mutation in Plasma of a NSCLC Patient

The assay tested two separate DNA extractions from plasma of a single NSCLC patient. Each extraction was digested with MseI and subsequently split into 11 separate PCR reactions. Two reactions yielded positive results as shown in Table 6 below.

TABLE 6

E746_A750del Mutation in the Plasma of a NSCLC Patient

| | | Peak Intensity | | | |
|---|---|---|---|---|---|
| | | 500 μl Plasma | | 350 μl Plasma | |
| Primer set | Aliquot # | 1:10 | Undiluted | 1:10 | Undiluted |
| E746_A750del | 1 | 0 | 0 | 53 | 163 |
| | 2 | 0 | 0 | 0 | 0 |
| | 3 | 3568 | 7952 | 0 | 0 |
| | 4 | 0 | 0 | 0 | 0 |
| | 5 | 0 | 0 | 0 | 0 |
| | 6 | 0 | 0 | 0 | 0 |
| | 7 | 0 | 0 | 0 | 0 |
| | 8 | 0 | 0 | 0 | 0 |
| | 9 | 3971 | 7359 | 0 | 0 |
| | 10 | 0 | 0 | 0 | 0 |
| | 11 | 0 | 0 | 2518 | 6469 |
| WT | 1 | 0 | — | 0 | — |

Example 5

DNA Extraction Comparison

Detection of rare mutations in plasma is a difficult feat and is dependant on both the ability to detect very low amounts of the mutation among large amounts of normal DNA and the ability to successfully recover the mutation from the patient plasma sample. Using a high quality DNA extraction method in conjunction with the methods and compositions provided herein, particularly combining non-target fragmentation with mutation specific primers further increases the ability to detect low copy target nucleic acid in patient samples, particularly plasma.

Figure 14:
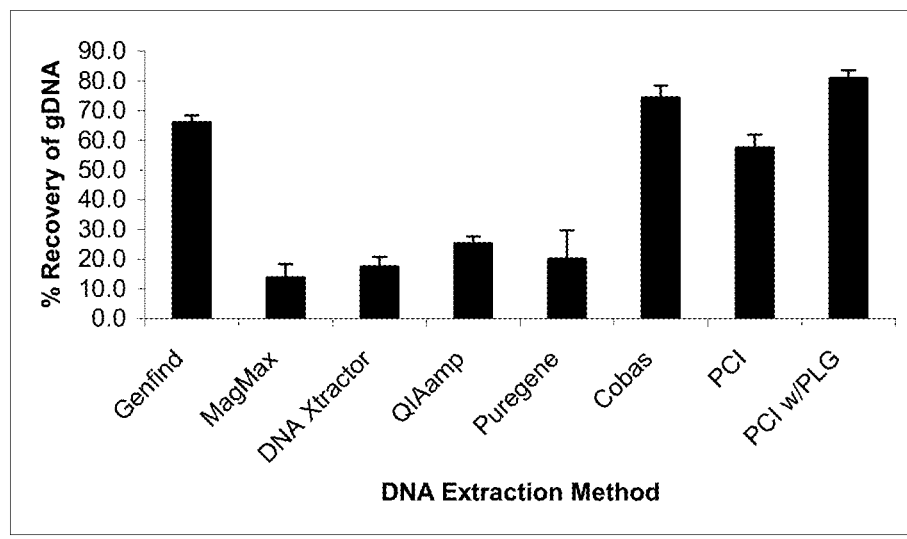
FIG. 14. Comparison of eight DNA extraction methods. Columns indicate the mean percent recovery of six plasma samples as described in Example 5.

To determine an optimal method of DNA extraction, eight DNA extraction methods were evaluated to find a method that is superior for obtaining high yield DNA as well as providing DNA that is amenable to the detection methods provided herein. Six plasma samples for each extraction method were spiked with various nucleic acids including every plasma sample being spiked with the EGFR exon 19 deletion (H1650 cell line gDNA) for subsequent evaluation of detection. All six plasma samples were extracted using the eight methods that included two lysis methods using magnetic bead based methods (Agencourt Genfind™ and Ambion MagMax™), two column based methods (Qiagen QIAmp DNA Blood Mini Kit and the automated Corbett DNA Xtractor™), two isopropanol precipitation based methods (Gentra Puregene™ and Roche Cobas®), and two phenol:chloroform based methods (standard method and with Eppendorf Phase Lock Gels®). The resulting yield was determined by picogreen fluorescent assay (Invitrogen Quant-iT™ PicoGreen® dsDNA Quantitation Assay) and the mean percent recovery of the six plasma samples was calculated for each method. Comparison of these eight DNA extraction methods revealed that three methods were clearly more efficient at DNA recovery than the other five (FIG. 14). These methods included Agencourt Genfind™, Roche Cobas® and phenol:chloroform extraction using Eppendorf Phase Lock Gels®.

Ambion MagMax™ is an isolation kit which can be used to isolate RNA or DNA from serum, plasma, or any other biofluid. Agencourt Genfind™ is a DNA isolation for blood, serum, or plasma samples. Both involve sample disruption with a lysis reagent followed by binding of the nucleic acid to magnetic beads (proprietary chemistry). The beads are then washed with a series of buffers to reduce and/or eliminate proteins and other contaminants from the sample in order to purify the nucleic acid. The nucleic acid is then eluted off the beads to yield the final DNA sample.

QIAamp DNA Blood Mini Kit and Corbett DNA Xtractor™ are both column based methods. The QIAamp procedure used in these studies was manual while the Corbett was an automated system. Both involve disruption of the sample with a lysis reagent followed by binding to a silica column. The column containing bound nucleic acid is washed with a series of wash buffers and the nucleic acid is then eluted in the last step with elution buffer to yield the final sample.

Gentra Puregene™ and Roche Cobas® methods are crude extractions and both incorporate treatment of plasma with a lysis reagent to disrupt the sample followed by isopropanol precipitation of DNA.

Phenol:Chloroform extraction involves separation of organic and aqueous phases of the plasma. The aqueous phase containing nucleic acid is isolated and re-extracted once more with phenol:chloroform. The aqueous phase is again isolated and the DNA is purified from this phase by isopropanol precipitation.

Phenol:Chloroform extraction using Phase Lock Gels® employs the phenol:chloroform procedure as described above, but once separated the aqueous and organic phases are separated by a solid gel. This allows increased recovery of the aqueous phase without contamination from the organic phase which can lead to inhibition of PCR.

Figure 15:
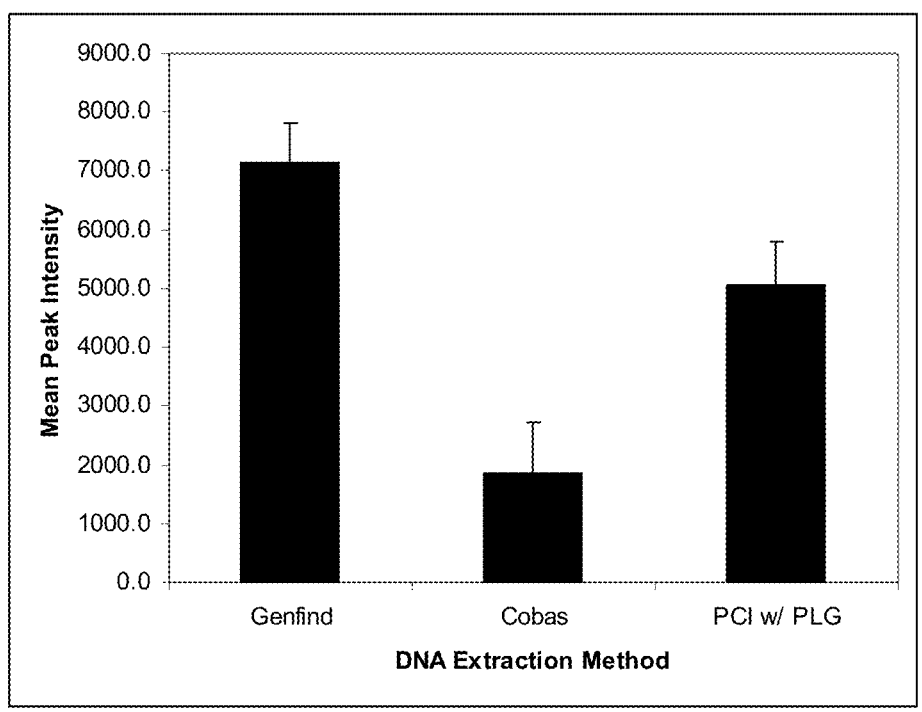
FIG. 15. Evaluation of detection between Agencourt Genfind™, Roche Cobas® and phenol:chloroform extraction using Eppendorf Phase Lock Gels® methods using spiked plasma samples as described in Example 5. Columns represent the mean peak intensity of E746_A750del PCR product from the six samples tested for each method obtained from an ABI 3100 Genetic Analyzer.

Further evaluations were performed to identify the best method from the three yielding the highest amounts of DNA. For this comparison, 18% of the final DNA sample from each extraction was subjected to our EGFR mutation detection assay as described in the Examples above. The mean peak intensity of the PCR products obtained corresponding to the E746_A750del EGFR mutation were calculated as an indicator of DNA quality and recovery of the spiked mutation (FIG. 15). Peak intensity values indicated that of the three methods tested, the Agencourt Genfind™ method provided the most robust amplification of spiked mutation.

Figure 16:
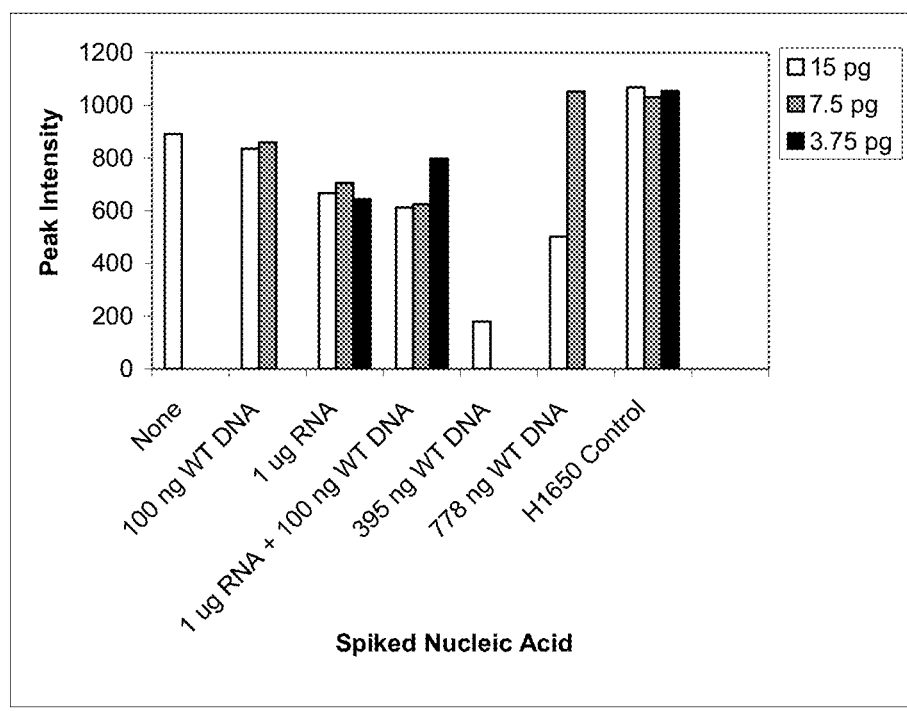
FIG. 16. Evaluation of nucleic acid spiking conditions as described in Example 5. Six nucleic acid carrier conditions include 1) no carrier, 2) no carrier plus 100 ng of normal DNA, 3) 1 µg of RNA carrier, 4) 1 µg of RNA carrier plus 100 ng of normal DNA, 5) 395 ng of normal DNA as a carrier, and 6) 778 ng of normal DNA as a carrier. Columns represent the mean peak intensity of E746_A750del PCR product.

Once the superior method was identified, further evaluation of the six nucleic acid carrier conditions was performed to determine if either condition facilitated recovery of the spiked mutation. These nucleic acid carrier conditions included use of RNA carrier or no carrier at low and high (100 nanograms (ng) spiked normal DNA) plasma DNA levels and the use of normal DNA as a carrier (395 ng and 778 ng). To determine optimal nucleic acid carrier conditions, dilutions of each sample were analyzed using our detection method. The concentration of mutant DNA in the extracted samples was first estimated based on the calculated percent recovery for each sample. The equivalent of 15 pg of H1650 DNA was used as the starting point and was further diluted 1:2 and 1:4. All three dilutions were analyzed for the presence of detectable spiked EGFR mutation. The samples employing RNA carrier were the only ones that detected the mutation in the 1:4 dilution indicating that spiking RNA carrier during the extraction facilitates recovery of the mutation present in the plasma sample (FIG. 16). FIG. 16 provides the results from evaluation of nucleic acid spiking conditions. The six nucleic acid carrier conditions include 1) no carrier, 2) no carrier plus 100 ng of normal DNA, 3) 1 µg of RNA carrier, 4) 1 µg of RNA carrier plus 100 ng of normal DNA, 5) 395 ng of normal DNA as a carrier, and 6) 778 ng of normal DNA as a carrier. Plasma samples spiked with 100 ng of normal DNA were included to represent patient plasma samples containing high amounts of DNA and were spiked immediately after thawing of the plasma sample. The two samples containing 395 ng and 778 ng of normal DNA were spiked following sample lysis during the extraction, the point at which nucleic acid carrier is to be added. Columns represent the mean peak intensity of E746_A750del PCR product.

The experiments performed in this study identified an optimal method for obtaining high yield DNA from plasma samples that is amenable to detection of rare mutations. This method was further improved by identifying nucleic acid spiking conditions that facilitate the recovery of mutations from the sample. Thus to improve the ability to recover rare mutations in the plasma and to successfully detect such mutations, it was determined that the Agencourt Genfind™ method with a modification to include addition of RNA carrier to the sample lysate is the choice method.

While Agencourt Genfind™ was the optimal extraction method in these experiments, any of the extraction methods tested can be used and are provide as exemplary extraction methods that can be used in conjunction with the methods and compositions provided herein. In different hands, results may vary, but all are acceptable methods.

Example 6

Detection Sensitivity of L858R in Wild-Type Background

DNA samples were initially digested with restriction enzymes (New England Biolabs) to cleave TTAA (MseI) and TGGCCA (MscI) recognition sites targeting wild type EGFR sequences (Mse I for singleplex E746_A750del; Msc I for singleplex L858R; Mse I and Msc I for multiplex reactions) for 2 hours at 37° C. followed by 20 minute inactivation at 65° C. Following restriction digestion, samples were amplified with AccuPrime™ Taq DNA Polymerase (Invitrogen) using E746_A750del and/or L858R mutation-specific primers (E746_A750del forward: 5'-[6FAM] CCC GTC GCT ATC AAA ACA TC-3' (SEQ ID NO:1); E746_A750del reverse: 5'-ATG TGG AGA TGA GCA GGG TCT-3' (SEQ ID NO:2); L858R forward: [6FAM] TCA CAG ATT TTG GGC GG-3' (SEQ ID NO:7); L858R reverse: CCT GGT GTC AGG AAA ATG CT-3' (SEQ ID NO:8)). In each set, the forward primer was labeled with 5'-6FAM. For added specificity, the L858R forward primer contained a locked nucleic acid (LNA) in the −1 position corresponding to the mutated base. Thermocycling conditions were as follows: denatured at 95° C. for 5 min; amplified with 40 cycles of 94° C. for 40 seconds, 55° C. (E746_A750del singleplex PCR) or 61.7° C. (L858R singleplex PCR and multiplex PCR) for 1 minute, 72° C. for 1 minute; final extension at 72° C. for 7 minutes. E746_A750del PCR product yielded an expected size of 153 bp and L858R PCR product yielded an expected size of 113 bp.

TABLE 7

Detection of L858R Mutation in the Background of Wild type EGFR.

| % L858R | Mean Peak Intensity[1] (110 bp)[2] |
|---|---|
| 0.001% | 463 |
| 0.0005% | 412 |
| 0.0003% | — |
| 0.0002% | — |
| 0% (2.5 ug/rxn) | — |

[1]Peak intensities <200 RFU are not reported
[2]Size represents observed L858R peak size on ABI 3100 Genetic Analyzer Several other mutation specific primers for detecting the L858R mutation were tested but were not effective in determining the presence of the mutant nucleic acid. The primers are provided in the table below:

TABLE 8

L858R Mutation Specific Primers.

| SEQ ID NO: | Primer Sequence | Mutant Base as a Locked Nucleic Acid (Yes or No) |
|---|---|---|
| 13 | ATCACAGATTTTGGGCG | Yes |
| 14 | CAAGATCACAGATTTTGGGCG | No |
| 15 | ATGTCAAGATCACAGATTTTGGGCG | No |
| 16 | AGATCACAGATTTTGGGCG | No |
| 17 | ATCACAGATTTTGGGCGG | No |
| 18 | TCACAGATTTTGGGCGGG | No |
| 19 | ATTTTGGGCGGGCCAAAC | No |
| 20 | AGATTTTGGGCGGGCCA | No |
| 21 | ATCACAGATTTTGGGCGG | Yes |

* The bolded underlined base is the location of the L858R mutant base.

Example 7

EGFR Mutation Detection in Paired Tissue and Plasma Samples

Paired FFPE tissue and plasma were obtained from 11 NSCLC donors with informed consent (10 from Indivumed, Hamburg, Germany; 1 from Good Samaritan Hospital, Kearney, Nebr.). DNA from FFPE tissue was analyzed by PCR followed by direct sequencing to determine mutation status of the paired tissue/plasma donors. One donor provided two plasma samples (856 and 3107) 1 year apart for analysis. In addition, 6 normal plasma samples and 5 plasma samples spiked with E746_A750del or L858R mutations were analyzed by the methods described herein.

Results of direct sequencing of FFPE tissue and multiplex fluorescent RF-PCR of plasma samples are presented in Table 3 along with tumor size and overall plasma DNA concentration. Overall 3/11 (27%) NSCLC donors had mutation positive FFPE tissue, while the remaining 8 were negative for the two mutations. Of the paired NSCLC samples, 83.3% (10/12) of plasma samples demonstrated identical mutation status to the matched FFPE tissue specimens. The two E746_A750del positive plasma samples were drawn from the same donor 1 year apart, thus 81.8% (9/11) unique donors had identical mutation status between paired samples. Notably, although the overall plasma DNA concentration had decreased by nearly half, the latter plasma specimen had twice as many positive wells as the specimen drawn 1 year previous (data not shown), suggesting the circulating mutation concentration had increased in that time.

For the mutation spiked plasma samples, 100% of samples spiked with 100, 200, and 300 pg of E746_A750del positive DNA (H1650 cell line) and 100% of samples spiked with 100 and 300 pg of L858R positive DNA (H1975 cell line) tested positive for their respective mutation. Furthermore, 6 normal plasma specimens tested negative for either mutation as expected.

TABLE 9

EGFR Mutation Detection in Paired Tissue and Plasma Samples

| Sample ID | Tumor Diameter (cm) | Plasma DNA Conc. (ng/mL) | EGFR Mutation Detected Tissue PCR/Direct Seq | Plasma RF-PCR |
|---|---|---|---|---|
| NSCLC | | | | |
| 856[1] | 6.5[2] | 15.6 | E746_A750del | E746_A750del |
| 3107[1] | 6.5[2] | 8.1 | E746_A750del | E746_A750del |
| 378 | 8.5 | 144 | — | — |
| 401 | 5 | 20.6 | — | — |
| 455 | 3.4 | 212 | — | — |
| 477 | 3.5 | 54.0 | — | — |
| 497 | 2.5 | 26.5 | L858R | — |
| 516 | 5.7 | 11.1 | — | — |
| 532 | 3.5 | 41.5 | — | — |
| 563 | 1.9 | 265 | L858R | — |
| 631 | 2.9 | 128 | — | — |
| 662 | 10.5 | 386 | — | — |
| E746_A750del Spiked | | | | |
| 200 pg | N/A | 23.3 | N/A | E746_A750del |
| 300 pg | N/A | 9.9 | N/A | E746_A750del |
| 100 pg | N/A | 7.6 | N/A | E746_A750del |
| L858R spiked | | | | |
| 300 pg | N/A | 8.0 | N/A | L858R |
| 100 pg | N/A | 6.4 | N/A | L858R |
| Normal | | | | |
| 4207 | N/A | 4.3 | N/A | — |
| 2011 | N/A | 5.8 | N/A | — |
| 2258 | N/A | 8.7 | N/A | — |
| 3391 | N/A | 7.4 | N/A | — |
| 975 | N/A | 4.4 | N/A | — |
| 725 | N/A | 7.1 | N/A | — |

[1]Sample IDs 856 and 3107 are from the same patient. Sample ID 3107 was drawn 1 year after Sample ID 856.
[2]Tumor size measured 4.7 years prior to initial draw and 5.7 years prior to second draw.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A kit comprising:
    an oligonucleotide primer pair comprising a forward primer of SEQ NO:1 and a reverse primer of SEQ NO:2 and restriction enzyme MseI;
    an oligonucleotide primer pair comprising a forward primer of SEQ NO:3 and a reverse primer of SEQ NO:4 and restriction enzyme MnlI;
    an oligonucleotide primer pair comprising a forward primer of SEQ NO:5 and a reverse primer of SEQ NO:6 and restriction enzyme MnlI;
    an oligonucleotide primer pair comprising a forward primer of SEQ NO:7 and a reverse primer of SEQ NO:8 and at least one restriction enzyme selected from MscI or EaeI, or a combination thereof;
    an oligonucleotide primer pair comprising a forward primer of SEQ NO:9 and a reverse primer of SEQ NO:10 and restriction enzyme FatI;
    an oligonucleotide primer pair comprising a forward primer of SEQ NO:11 and a reverse primer of SEQ NO:12 and restriction enzyme HpyCH4VI; or
    a combination thereof;
    at least one oligonucleotide of the primer pair is labeled with a detectable moiety.

2. The kit of claim 1, wherein the detectable moiety is a fluorescent dye.

3. The kit of claim 1, wherein different pairs of primers in the kit are labeled with different distinguishable detectable moieties.

4. The kit of claim 1, wherein the at least one primer pair comprises a forward primer and a reverse primer labeled with different detectable moieties.

5. The kit of claim 1, wherein the kit comprises the oligonucleotide primer pair SEQ ID NOs: 1 and 2 and the restriction enzyme MseI.

6. The kit of claim 1, wherein the kit comprises the oligonucleotide primer pair SEQ ID NOs: 3 and 4 and the restriction enzyme MnlI.

7. The kit of claim 1, wherein the kit comprises the oligonucleotide primer pair SEQ ID NOs: 5 and 6 and the restriction enzyme MnlI.

8. The kit of claim 1, wherein the kit comprises the oligonucleotide primer pair SEQ ID NOs: 7 and 8 and the restriction enzyme MscI or EaeI, or a combination thereof.

9. The kit of claim 1, wherein the kit comprises the oligonucleotide primer pair SEQ ID NOs: 9 and 10 and the restriction enzyme FatI.

10. The kit of claim 1, wherein the kit comprises the oligonucleotide primer pair SEQ ID NOs: 11 and 12 and the restriction enzyme HpyCH4VI.

* * * * *

SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cccgtcgcta tcaaaacatc                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgtggagat gagcagggtc t                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cttccacaat ggttgaacta g                                                  21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catccatgtc cctacaaagg                                                    20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagccattta tacagaaaga tg                                                 22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaataccat ttgacccagc                                                    20

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcacagattt tgggcgg                                                17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctggtgtca ggaaaatgct                                             20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgagctaagc aggaggcgg                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtccatagtc gctggaggag                                             20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgagctaagc aggaggcgg                                              19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actttcagcc tgatagtctg g                                           21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
atcacagatt ttgggcg                                                    17

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
caagatcaca gattttgggc g                                               21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
atgtcaagat cacagatttt gggcg                                           25

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agatcacaga ttttgggcg                                                  19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
atcacagatt tgggcgg                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tcacagattt tgggcggg                                                   18

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
attttgggcg ggccaaac                                                  18

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agattttggg cgggcca                                                   17

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcacagatt ttgggcgg                                                  18

<210> SEQ ID NO 22
<211> LENGTH: 770
<212> TYPE: DNA
<213> ORGANISM: Homo sapiens

<400> SEQUENCE: 22
ccacacggac tttataacag gctttacaag cttgagattc ttttatctaa ataatcagtg     60
tgattcgtgg agcccaacag ctgcagggct gcggggcgt cacagccccc agcaatatca    120
gccttaggtg cggctccaca gccccagtgt ccctcacctt cggggtgcat cgctggtaac    180
atccacccag atcactgggc agcatgtggc accatctcac aattgccagt taacgtcttc    240
cttctctctc tgtcatagg actctggatc ccagaaggtg agaaagttaa aattcccgtc    300
gctatcaagg aattaagaga agcaacatct ccgaaagcca acaaggaaat cctcgatgtg    360
agtttctgct ttgctgtgtg ggggtccatg gctctgaacc tcaggcccac cttttctcat    420
gtctggcagc tgctctgctc tagaccctgc tcatctccac atcctaaatg ttcactttct    480
atgtctttcc ctttctagct ctagtgggta taactccctc cccttagaga cagcactggc    540
ctctcccatg ctggtatcca ccccaaaagg ctggaaacag gcaattactg gcatctaccc    600
agcactagtt tcttgacacg catgatgagt gagtgctctt ggtgagcctg gagcatgggt    660 attgttttg gtattttttg gatgaagaaa tggaggcata agaaattgg ctgaccctta     720 tatggctggg atagggttta agccccttgt tatttctgac tctgaaactt                770

<210> SEQ ID NO 23
<211> LENGTH: 755
<212> TYPE: DNA
<213> ORGANISM: Homo sapiens

<400> SEQUENCE: 23
```

```
ccacacggac tttataacag gctttacaag cttgagattc ttttatctaa ataatcagtg      60
tgattcgtgg agcccaacag ctgcagggct gcggggggcgt cacagccccc agcaatatca    120
gccttaggtg cggctccaca gccccagtgt ccctcacctt cggggtgcat cgctggtaac    180
atccacccag atcactgggc agcatgtggc accatctcac aattgccagt taacgtcttc    240
cttctctctc tgtcataggg actctggatc ccagaaggtg agaaagttaa aattcccgtc    300
gctatcaaaa catctccgaa agccaacaag gaaatcctcg atgtgagttt ctgctttgct    360
gtgtgggggt ccatggctct gaacctcagg cccaccttt tctcatgtctg cagctgctc    420 tgctctagac cctgctcatc tccacatcct aaatgttcac tttctatgtc tttcccttc    480 tagctctagt gggtataact ccctcccctt agagacagca ctggcctctc ccatgctggt    540
atccacccca aaaggctgga acaggcaat tactggcatc tacccagcac tagtttcttg    600
acacgcatga tgagtgagtg ctcttggtga gcctggagca tgggtattgt ttttggtatt    660
ttttggatga agaaatggag gcataaagaa attggctgac ccttatatgg ctgggatagg    720
gtttaagccc cttgttattt ctgactctga aactt                               755

<210> SEQ ID NO 24
<211> LENGTH: 1562
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24
ccagctccgt tcagagtgaa ccatgcagtg gaatggtaag tggcattata agccccagtg     60
atcttccaga tagccctgga caaaccatgc caccaagcag aagtaaaaca cctccaccac    120
ctcctcaaac agctcaaacc aagcgagaag tacctaaaaa taaagcacct actgctgaaa    180
agagagagag tggacctaag caagctgcag taaatgctgc agttcagagg gtccaggttc    240
ttccagatgc tgatacttta ttacattttg ccacggaaag tactccagat ggattttctt    300
gttcatccag cctgagtgct ctgagcctcg atgagccatt tatacagaaa gatgtggaat    360
taagaataat gtgcatgtgt ctttatagca gcatgattta tactcatttg ggtatatacc    420
cagtaatggg atggctgggt caaatggtat ttctagttct agatccctga ggaatcgcca    480
cactgacttc cacaatggtt gaactagttt acagtcccac caagaaaatg tggcacatat    540
acaccatgga atactatgca gccataaaaa atgatgagtt catatccttt gtagggacat    600
ggatgaaatt ggaaaccatc attctcagta aactatcgca agaacaaaaa accaaacacc    660
gcatattctc acttataggt gggaattgaa caatgagatc acatggacac aggaagggga    720
atatcacact ctggggactg tggtgggtc gggggagggg ggagggatag cattgggaga    780
tatacctaat gctagatgac acattagtgg gtgcagcgca gcatggcaca tgtatacata    840
tgtaactaac ctgcacaatg tgcacatgta ccctaaaact tagagtataa taaaaaaaaa    900
aaaaaaaaaa ataacaataa atgagataaa atctaaaaaa aaaaaaaaa aaaaaaaaa    960 aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa agaataatgc ctccagttca   1140
ggaaaatgac aatgggaatg aaacagaatc agagcagcct aaagaatcaa atgaaaacca   1200
agagaaagag gcagaaaaaa ctattgattc tgaaaaggac ctattagatg attcagatga   1260
```

| | |
|---|---|
| tgatgatatt gaaatactag aagaatgtat tatttctgcc atgccaacaa agtcatcacg | 1320 |
| taaagcaaaa aagccagccc agactgcttc aaaattacct ccacctgtgg caaggaaacc | 1380 |
| aagtcagctg cctgtgtaca aacttctacc atcacaaaac aggttgcaac cccaaaagca | 1440 |
| tgttagtttt acaccggggg atgatatgcc acgggtgtat tgtgttgaag ggacacctat | 1500 |
| aaacttttcc acagctacat ctctaagtga tctaacaatc gaatcccctc caaatgagtt | 1560 |
| ag | 1562 |

<210> SEQ ID NO 25
<211> LENGTH: 1562
<212> TYPE: DNA
<213> ORGANISM: Artificial Sequence
<220> FEATURE:
<223> OTHER INFORMATION: Description of Artificial Sequence: Synthetic construct

<400> SEQUENCE: 25

| | |
|---|---|
| ccagctccgt tcagagtgaa ccatgcagtg gaatggtaag tggcattata agccccagtg | 60 |
| atcttccaga tagccctgga caaaccatgc caccaagcag aagtaaaaca cctccaccac | 120 |
| ctcctcaaac agctcaaacc aagcgagaag tacctaaaaa taaagcacct actgctgaaa | 180 |
| agagagagag tggacctaag caagctgcag taaatgctgc agttcagagg gtccaggttc | 240 |
| ttccagatgc tgatacttta ttacattttg ccacggaaag tactccagat ggattttctt | 300 |
| gttcatccag cctgagtgct ctgagcctcg atgagccatt tatacagaaa gatgtggaat | 360 |
| taagaataat gtgcatgtgt ctttatagca gcatgattta tactcatttg ggtatatacc | 420 |
| cagtaatggg atggctgggt caaatggtat ttctagttct agatccctga ggaatcgcca | 480 |
| cactgacttc cacaatggtt gaactagttt acagtccac caagaaaatg tggcacatat | 540 |
| acaccatgga atactatgca gccataaaaa atgatgagtt catatccttt gtagggacat | 600 |
| ggatgaaatt ggaaaccatc attctcagta aactatcgca agaacaaaaa accaaacacc | 660 |
| gcatattctc acttataggt gggaattgaa caatgagatc acatggacac aggaagggga | 720 |
| atatcacact ctggggactg tggtggggtc ggggagggg ggaggatag cattgggaga | 780 |
| tatacctaat gctagatgac acattagtgg gtgcagcgca gcatggcaca tgtatacata | 840 |
| tgtaactaac ctgcacaatg tgcacatgta ccctaaaact tagagtataa taaaaaaaaa | 900 |
| aaaaaaaaaa ataacaataa atgagataaa atctaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa agaataatgc ctccagttca | 1140 |
| ggaaaatgac aatgggaatg aaacagaatc agagcagcct aaagaatcaa atgaaaacca | 1200 |
| agagaaagag gcagaaaaaa ctattgattc tgaaaggac ctattagatg attcagatga | 1260 |
| tgatgatatt gaaatactag aagaatgtat tatttctgcc atgccaacaa agtcatcacg | 1320 |
| taaagcaaaa aagccagccc agactgcttc aaaattacct ccacctgtgg caaggaaacc | 1380 |
| aagtcagctg cctgtgtaca aacttctacc atcacaaaac aggttgcaac cccaaaagca | 1440 |
| tgttagtttt acaccggggg atgatatgcc acgggtgtat tgtgttgaag ggacacctat | 1500 |
| aaacttttcc acagctacat ctctaagtga tctaacaatc gaatcccctc caaatgagtt | 1560 |
| ag | 1562 |

<210> SEQ ID NO 26
<211> LENGTH: 39
<212> TYPE: DNA
<213> ORGANISM: Homo sapiens

<400> SEQUENCE: 26
cagcatgtca agatcacaga ttttgggctg gccaaactg                          39

<210> SEQ ID NO 27
<211> LENGTH: 39
<212> TYPE: DNA
<213> ORGANISM: Homo sapiens

<400> SEQUENCE: 27
cagcatgtca agatcacaga ttttgggcgg gccaaactg                          39

<210> SEQ ID NO 28
<211> LENGTH: 524
<212> TYPE: DNA
<213> ORGANISM: Homo sapiens

<400> SEQUENCE: 28
tgaccctgaa ttcggatgca gagcttcttc ccatgatgat ctgtccctca cagcagggtc    60
ttctctgttt cagggcatga actacttgga ggaccgtcgc ttggtgcacc gcgacctggc   120
agccaggaac gtactggtga aaacaccgca gcatgtcaag atcacagatt ttgggctggc   180
caaactgctg ggtgcggaag agaaagaata ccatgcagaa ggaggcaaag taaggaggtg   240
gctttaggtc agccagcatt ttcctgacac cagggaccag gctgccttcc cactagctgt   300
attgtttaac acatgcaggg gaggatgctc tccagacatt ctgggtgagc tcgcagcagc   360
tgctgctggc agctgggtcc agccagggtc tcctggtagt gtgagccaga gctctgaggt   420
ttcactctgg cctgctgggc tcctagcagc caccaaccca tgatgctggg ccctgaaaac   480
acacgcagac ctggatgagt gaggccactg gcacaaccca gggc                   524

<210> SEQ ID NO 29
<211> LENGTH: 413
<212> TYPE: DNA
<213> ORGANISM: Homo sapiens

<400> SEQUENCE: 29
tgaccctgaa ttcggatgca gagcttcttc ccatgatgat ctgtccctca cagcagggtc    60
ttctctgttt cagggcatga actacttgga ggaccgtcgc ttggtgcacc gcgacctggc   120
agccaggaac gtactggtga aaacaccgca gcatgtcaag atcacagatt ttgggcgggc   180
caaactgctg ggtgcggaag agaaagaata ccatgcagaa ggaggcaaag taaggaggtg   240
gctttaggtc agccagcatt ttcctgacac cagggaccag gctgccttcc cactagctgt   300
attgtttaac acatgcaggg gaggatgctc tccagacatt ctgggtgagc tcgcagcagc   360
tgctgctggc agctgggtcc agccagggtc tcctggtagt gtgagccaga gct         413

<210> SEQ ID NO 30
<211> LENGTH: 316
<212> TYPE: DNA
<213> ORGANISM: Homo sapiens

<400> SEQUENCE: 30
tgtcgccctg accctggga caccgcctcc tgagattaaa gcgagagcca gggcgggccg    60
ggccgagtag gcgcgagcta agcaggaggc ggaggcggag gcggagggcg aggggcgggg   120

```
agcgccgcct ggagcgcggc aggtcatatt gaacattcca gatacctatc attactcgat    180
gctgttgata acagcaagat ggctttgaac tcagggtcac caccagctat tggaccttac    240
tatgaaaacc atggatacca accggaaaac ccctatcccg cacagcccac tgtggtcccc    300
actgtctacg aggtgc                                                    316

<210> SEQ ID NO 31
<211> LENGTH: 364
<212> TYPE: DNA
<213> ORGANISM: Homo sapiens

<400> SEQUENCE: 31
ccaaaagcaa gacaaatgac tcacagagaa aaagatggc agaaccaagg gcaactaaag      60
ccgtcaggtt ctgaacagct ggtagatggg ctggcttact gaaggacatg attcagactg    120
tcccggaccc agcagctcat atcaaggaag cctatcagt tgtgagtgag gaccagtcgt    180
tgtttgagtg tgcctacgga acgccacacc tggctaagac agagatgacc gcgtcctcct    240
ccagcgacta tggacagact tccaagatga gcccacgcgt ccctcagcag gattggctgt    300 ctcaacccc agccagggtc accatcaaaa tggaatgtaa ccctagccag gtgaatggct     360
caag                                                                364

<210> SEQ ID NO 32
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 32
tgtcgccctg gaccctggga caccgcctcc tgagattaaa gcgagagcca gggcgggccg     60
ggccgagtag gcgcgagcta agcaggaggc ggaggcggag gcggagggcg aggggcgggg    120
agcgccgcct ggagcgcggc aggaagcctt atcagttgtg agtgaggacc agtcgttgtt    180
tgagtgtgcc tacggaacgc cacacctggc taagacagag atgaccgcgt cctcctccag    240
cgactatgga cagacttcca agatgagccc acgcgtccct cagcaggatt ggctgtctca    300
acccccagcc agggtcacca tcaaaatgga atgtaaccct agccaggtga atggctcaag    360

<210> SEQ ID NO 33
<211> LENGTH: 316
<212> TYPE: DNA
<213> ORGANISM: Homo sapiens

<400> SEQUENCE: 33
tgtcgccctg gaccctggga caccgcctcc tgagattaaa gcgagagcca gggcgggccg     60
ggccgagtag gcgcgagcta agcaggaggc ggaggcggag gcggagggcg aggggcgggg    120
agcgccgcct ggagcgcggc aggtcatatt gaacattcca gatacctatc attactcgat    180
gctgttgata acagcaagat ggctttgaac tcagggtcac caccagctat tggaccttac    240
tatgaaaacc atggatacca accggaaaac ccctatcccg cacagcccac tgtggtcccc    300
actgtctacg aggtgc                                                   316

<210> SEQ ID NO 34
<211> LENGTH: 355
<212> TYPE: DNA
<213> ORGANISM: Homo sapiens
```

```
<400> SEQUENCE: 34
tgcgaagagc agcagcatgg atggatttta tgaccagcaa gtgccttaca tggtcaccaa      60
tagtcagcgt gggagaaatt gtaacgagaa accaacaaat gtcaggaaaa gaaaattcat    120
taacagagat ctggctcatg attcagaaga actctttcaa gatctaagtc aattacagga    180
aacatggctt gcagaagctc aggtacctga caatgatgag cagtttgtac cagactatca    240
ggctgaaagt ttggcttttc atggcctgcc actgaaaatc aagaaagaac cccacagtcc    300
atgttcagaa atcagctctg cctgcagtca agaacagccc tttaaattca gctat         355

<210> SEQ ID NO 35
<211> LENGTH: 300
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35
tgtcgccctg daccctggga caccgcctcc tgagattaaa gcgagagcca gggcgggccg      60
ggccgagtag gcgcgagcta agcaggaggc ggaggcggag gcggagggcg aggggcgggg    120
agcgccgcct ggagcgcggc agctcaggta cctgacaatg atgagcagtt tgtaccagac    180
tatcaggctg aaagtttggc ttttcatggc ctgccactga aaatcaagaa agaaccccac    240
agtccatgtt cagaaatcag ctctgcctgc agtcaagaac agccctttaa attcagctat    300
```